United States Patent
White et al.

(10) Patent No.: US 7,062,385 B2
(45) Date of Patent: Jun. 13, 2006

(54) INTELLIGENT ELECTRO-OPTICAL NUCLEIC ACID-BASED SENSOR ARRAY AND METHOD FOR DETECTING VOLATILE COMPOUNDS IN AMBIENT AIR

(75) Inventors: Joel E. White, Millis, MA (US); John S. Kauer, Weston, MA (US)

(73) Assignee: Tufts University, Boston, MA (US)

( * ) Notice: Subject to any disclaimer, the term of this patent is extended or adjusted under 35 U.S.C. 154(b) by 0 days.

(21) Appl. No.: 10/303,548

(22) Filed: Nov. 25, 2002

(65) Prior Publication Data

US 2004/0101851 A1 May 27, 2004

(51) Int. Cl.
- *A01N 43/04* (2006.01)
- *G01N 1/22* (2006.01)
- *G01N 9/00* (2006.01)
- *G01N 19/10* (2006.01)

(52) U.S. Cl. ............... 702/23; 436/122; 422/82.06; 422/82.08; 73/23.2; 73/31.1

(58) Field of Classification Search ............... 436/172; 422/82.06, 82.08; 702/23; 73/31.1, 23.2
See application file for complete search history.

(56) References Cited

U.S. PATENT DOCUMENTS 6,649,403 B1* 11/2003 McDevitt et al. ......... 435/288.5
6,649,416 B1 11/2003 Kauer et al.

OTHER PUBLICATIONS

Aathithan et al., *J. Clin. Microbiol.*, 39(7):2590-2593 (2001).
Alkasab et al., *Chem. Senses*, 27:261-275 (2001).
Bouche et al., *J. Anal. Toxicol.*, 26:35-42 (2001).
Cam D. and Gagni, S., *J. Chromatogr. Sci.*, 39:481-486 (2001).
Cancho et al., *J. Chromatogr.*, 943:1-13 (2001).
Christensen, Thomas A. and White, Joel, *Neurobiology of Taste and Smell*, 2nd. Ed.: 201-203 (2000).
Dickinson et al., *Trends Biotechnol.*, 16:250-258 (1998).
Finger, Thomas E. and Silver, Wayne L., *Neurobiology of Taste and Smell*, pp. 201-231, John Wiley & Sons, New York (1987).
Freund, Michael S. and Lewis, Nathan S., *Proc.Nat. Acad. Sci. USA*, 92:2652-2656 (1995).
Gardner, Julian W. and Bartlett, Philip N., *Kluwer Academic Publishers*, Sensors and Sensory for an Electronic Nose, 161-179, 197-236 (1992).
Gardner Julian W. and Bartlett, Philip N., *Sensors and Actuators B*, 18-19:211-220 (1994).
Gardner, Julian W. and Hines, Evor L, *CRS Press. Inc.*, Pattern Analysis Techniques, pp. 633-652 (1997).
Grate et al., *Anal. Chem.*, 65:1868-1881 (1993).
Grote, Christoph and Pawliszyn, Tanusz, *Anal. Chem.*, 69:587-596 (1997).
Jenkins et al., *Talanta*, 54:501-513 (2001).
Kauer, John S., *Trends Neurosci*, 14:79-85 (1991).
Kent, Paul F. and Mozell, Maxwell M., *J. Neurophysiol*, 6(5): 1804-1819 (1992).
Lambropoulou, Dimitra A. and Albanis, Triantafyllos A., *J. Chromatogr.*, 922:243-255 (2001).
Lu et al., *Physiol. Behav.*, 53:795-804 (1993).
Mackay-Sim et al., *J. Neurophysiol.*, 48(2):584-596 (1982).
Mosaddegh et al., *Ann. Clin. Biochem.*, 38:541-547 (2001).
Musshoff et al., *J. Chromatogr. Sci.*, 40:29-34 (2002).
Passe, D.H. and Walker, J.C., *Neurosci. & Biobehav. Rev.*, 9:431-467 (1985).
Persaud, Krishna and Dodd, George, *Nature*, 299:352-355 (1982).
Phillips et al., *Lancet*, 353:1930-1933 (1999).
Ping et al., *Biosens. & Bioelectron.*, 12(9-10):1031-1036 (1997).
Schneider et al., *J. Chromatogr. Sci.*, 39:420-424 (2001).
Slotnick et al., *Physiol. & Behav.*, 50:555-561 (1991).
Stojanovic et al., *J. Am. Chem. Soc.*, 122: 11547-11548 (2000).
White, Joel and Kauer, John S., *Anal. Chem.*, 68:2191-2202 (1996).
Yamazaki et al., *Genetica*, 104:235-240 (1999).
Youngentob et al., *Physiol. & Behav.*, 47:1053-1059 (1990).
Zhang et al., *Anal. Chem.*, 66:844A-852A (1994).
Database Caplus On STN. DN 134:175042. Stojanovic et al. "Fluorescent Sensors Based on Aptamer Self-Assembly". Journal of the American Chemical Society, 2000, vol. 122, No. 46, pp. 11547-11548.

* cited by examiner

Primary Examiner—Michael Borin
(74) Attorney, Agent, or Firm—David S. Resnick; Nixon Peabody, LLP

(57) ABSTRACT

The present invention generally relates to nucleic acid-based sensors and methods for detecting volatile analytes. More particularly, this invention relates to nucleic acid-based optical sensors, sensor arrays, sensing systems and sensing methods for intelligent sensing and detection of unknown materials by way of real-time feedback and control of sampling conditions.

8 Claims, 23 Drawing Sheets

INTELLIGENT ELECTRO-OPTICAL NUCLEIC ACID-BASED SENSOR ARRAY AND METHOD FOR DETECTING VOLATILE COMPOUNDS IN AMBIENT AIR

GOVERNMENT SUPPORT

This invention was made with government support under DC00228 awarded by the National Institutes of Health, N00014-95-1-1340 awarded by the Office of Naval Research, and DAAK60-97-K-9502 awarded by the Army. The government has certain rights in the invention.

FIELD OF THE INVENTION

This invention generally relates to nucleic acid-based sensors and methods for detecting volatile analytes. More particularly, this invention relates to nucleic acid-based optical sensors, sensor arrays, sensing systems and sensing methods for intelligent sensing and detection of unknown materials by way of real-time feedback and control of sampling conditions.

BACKGROUND OF THE INVENTION

There are a number of other current and potential uses for detection and identification of volatile compounds. For example, different chemical analyses have been used to detect the presence or absence of a known target chemical in clinical diagnoses, to identify unknown compounds and mixtures in basic research and drug discovery, and to document the identity and purity of known compounds, e.g., in testing and quality control in drug manufacturing processes. In addition to laboratory analyses, chemical detection is also important outside of the laboratory. Examples include bedside diagnoses, and environmental monitoring for hazardous materials. The "field" applications, including detection of explosives and chemical warfare agents, require small, portable, reliable, easy-to-use, inexpensive devices.

The serious threat of explosive, chemical and/or biological attacks pose a particular challenge for national security in the current "post September 11th" era. A method that could detect a wide range of compounds, and that could also be automated and remotely controlled and that could be used in field conditions including airport, seaport, or other screening systems, would be particularly desirable. For example, currently only about 2% of all the containers are screened by any means that come through the seaports to the United States, because there are no suitable reliable, fast, easy and relatively cheap screening methods available. For national security, it is imperative to develop screening methods that could detect, for example, explosives and toxic chemicals that may be transported into the United States. Detection methods for identifying trace amounts of volatile compounds from, for example, explosives or chemical warfare agents, would be one possible way to approach such novel screening methods for national security purposes.

There are a number of methods currently available for chemical analysis, each appropriate for a particular application and each having its own strengths and weaknesses. Examples include the various forms of chromatography, including gas chromatography (GC), high performance liquid chromatography (HPLC), and spectroscopy, including mass spectroscopy (MS), ion mobility spectroscopy (IMS), Raman spectroscopy and infrared spectroscopy, as well as other chemical, immunological, and gravimetric methods. Also, combinations of different methods can provide a powerful means of identifying unknown compounds, e.g., GC/MS which is used extensively in analytical chemistry laboratories.

A common feature of these analytical methods is that the chemical sample needs to be prepared prior to analysis. Liquid and solid samples are usually dissolved into an appropriate solvent. For analysis of vapor-phase chemicals, a preconcentration step is often required to increase the quantity of material for analysis.

Preconcentration of vapor-phase chemicals involves, for example, passing a large volume of air over an adsorbent Tenax or solid phase microextraction (SPME) trap. The sample is removed from the trap using a small amount of liquid solvent or is thermally desorbed directly into the input of a GC for analysis (Zhang, Z., Yang, M. J., and Pawliszyn, J. (1994). *Anal. Chem.*, 66:844A–853A).

Preconcentration followed by GC or GC/MS has been used to detect and quantify volatile chemicals in a variety of studies with relevance to health care and domestic security, for example, detection of contaminants in water (Lambropoulou, D. A. and Albanis, T. A. (2001). *J. Chromatogr.*, 922:243–255; Cancho, B., Ventura, F., and Galceran, M. T. (2002). *J. Chromatogr.*, 943:1–13) and soils (Cam, D. and Gagni, S. (2001). *J. Chromatogr. Sci.*, 39:481–486), detection of toxic substances in blood (Bouche, M. P., Lambert, W. E., Bocxlaer, J. F. V., Piette, M. H., and Leenheer, A. P. D. (2001). *J. Anal. Toxicol.*, 26:35–42; Musshoff, F., Junker, H., and Madea, B. (2002). *J. Chromatogr. Sci.*, 40:29–34), detection of drugs in postmortem tissue (Mosaddegh, M. H., Richardson, R., Stoddart, R. W., and McClure, J. (2001). *Ann. Clin. Biochem.*, 38:541–547), detection of organic compounds in normal breath (Grote, C. and Pawliszyn, J. (1997). *Anal. Chem.*, 69:587–596) and in the breath of lung cancer patients (Phillips, M., Gleeson, K., Hughes, J. M. B., Greenberg, J., Cataneo, R. N., Baker, L., and McVay, W. P. (1999). *Lancet*, 353:1930–1933), characterization of explosive signatures (Jenkins, T. F., Leggett, D. C., Miyares, P. H., Walsh, M. E., Ranney, T. A., Cragin, J. H., and George, V. (2001). *Talanta*, 54:501–513), and detecting Sarin in air and water (Schneider, J. F., Boparai, A. S., and Reed, L. L. (2001). *J. Chromatogr. Sci.*, 39:420–424). For rapid detection of volatile compounds, it would be advantageous to avoid specific sample preparation steps. This would be especially desirable in applications where detection is performed in field conditions, outside a laboratory.

Volatile chemical analyses using these methods require optimizations for each analysis problem. For example, the GC column, GC detector, trap coatings, and flow rates all need to be optimized for particular volatiles of interest. In addition, preconcentration can take considerable time to collect sufficient material in the trap. The time required depends on the sorbent coating on the trap (different Tenax coatings have different affinities for different chemical compounds) and on the original concentration of sample in the air. Such analytical methods are therefore generally inappropriate for rapid analyses, such as security screening, real-time environmental monitoring, or bedside diagnoses. Therefore, it would be advantageous to develop a detection system that is capable of rapidly analyzing a wide array of different compounds in varying concentrations.

For air sampling, an alternative to preconcentration consists of systems containing dedicated sensors that are responsive to particular compounds of interest. Common examples include home detectors for carbon monoxide, propane, and natural gas. Although sensors are available that are broadly responsive, e.g., sensors that respond to many volatile organic compounds, these devices do not identify the vapor detected. While a system containing a dedicated sensor can respond rapidly and may not require preconcentration, the ability to detect and identify multiple volatile compounds would require a separate sensor selective for each compound of interest. Further, such methods preclude detection of future compounds of interest. Therefore, it would be desirable to develop a system that is capable of sensing as well as identifying a wide range of compounds.

For detecting, discriminating, and identifying volatile compounds in the air, one of the most highly developed chemical detection devices is arguably the olfactory system of terrestrial animals. Olfactory abilities include high sensitivity (Passe, D. H. and Walker, J. C. (1985). *Neurosci. Biobehav. Rev.,* 9:431–467), the ability to detect and discriminate many different compounds (e.g., Youngentob, S. L., Markert, L. M., Mozell, M. M., and Hornung, D. E. (1990). *Physiol. Behav.,* 47:1053–1059; Slotnick, B. M., Kufera, A., and Silberberg, A. M. (1991). *Physiol. Behav.,* 50:555–561; Lu, X.-C. M., Slotnick, B. M., and Silberberg, A. M. (1993). *Physiol. Behav.,* 53:795–804), and the ability to make fine odorant discriminations (e.g., individual recognition in rodents—Yamazaki, K., Singer, A., and Beauchamp, G. K. (1998–1999). *Genetica,* 104:235–240). Numerous mechanisms influence these capabilities at points in the process even before odorant molecules interact with receptor proteins. Sniffing behavior, nasal aerodynamics, mucus solvation, and odorant clearing all likely play a role in olfactory abilities (Christensen, T. A. and White, J. (2000). Representation of olfactory information in the brain. In Finger, T. E., Silver, W. L., and Restrepo, D., editors, *Neurobiology of Taste and Smell,* pages 201–232. John Wiley & Sons, New York). Once odorants reach the olfactory receptor proteins in the nasal mucosa, the system does not devote one receptor protein to each individual odorous ligand. Rather, even single compounds interact with many broadly-responsive receptor proteins, producing widespread spatiotemporal patterns of activity in the olfactory sensory neuron population—in other words, activity in many sensor elements that evolve over time (MacKay-Sim, A., Shaman, P., and Moulton, D. G. (1982). *J. Neurophysiol.,* 48:584–596; Kent, P. F. and Mozell, M. M. (1992). *J. Neurophysiol,* 68:1804–1819). These patterns of activity are then interpreted by parallel processing elements in the olfactory areas of the brain, producing widespread activation in the neuronal populations at each level of the olfactory pathway (for reviews, see Kauer, 1987 Kauer, J. S. (1987). Coding in the olfactory system. In Finger, T. E. and Silver, W. L., editors, *Neurobiology of Taste and Smell,* pages 205–231. John Wiley & Sons, Inc, New York; Kauer, J. S. (1991). *Trends Neurosci,* 14:79–85; Christensen, T. A. and White, J. (2000). Representation of olfactory information in the brain. In Finger, T. E., Silver, W. L., and Restrepo, D., editors, *Neurobiology of Taste and Smell,* pages 201–232. John Wiley & Sons, New York).

The properties of the olfactory system suggest that engineered devices based on olfactory mechanisms may have advantages for detecting and identifying volatile compounds. Such a device, called an "artificial nose" or "electronic nose," was first described in the early 1980's (Persaud, K. and Dodd, G. (1982). *Nature,* 299:352–355), and a number of systems have been reported since then (see, e.g., Grate, J. W., Rose-Pehrsson, S. L., Venezky, D. L., Klusty, M., and Wohltjen, H. (1993). *Anal. Chem.,* 65:1868–1881; Freund, M. S. and Lewis, N. S. (1995). *Proc. Nat. Acad. Sci. USA,* 92:2652–2656; White, J., Kauer, J. S., Dickinson, T. A., and Walt, D. R. (1996). *Anal. Chem.,* 68:2191–2202). All of these devices incorporate the two main features that define an electronic nose: 1) an array of broadly-responsive sensors and 2) a pattern recognition method for processing sensor output. Like in the olfactory system, odorants interact with multiple sensors, producing a pattern of activation across the array. Commercial and research electronic noses use a variety of technologies for chemical sensing including conducting polymers, surface acoustic wave devices, solid-state devices, and optical interrogation. Pattern recognition methods generally involve statistical methods or computational neural networks (for reviews, see Gardner, J. W. and Bartlett, P. N., editors (1992). *Sensors and sensory systems for an electronic nose.* Kluwer Academic Publishers, Dordrecht, The Netherlands; Gardner, J. W. and Bartlett, P. N. (1994). *Sensors and Actuators B,* 18–19:211–220; Gardner, J. W. and Hines, E. L. (1997). Pattern analysis techniques. In Kress-Rogers, E., editor, *Handbook of Biosensors and Electronic Noses: Medicine, Food, and the Environment,* pages 633–652. CRC Press, Boca Raton, Fla.; Dickinson, T. A., White, J., Kauer, J. S., and Walt, D. R. (1998). *Trends Biotechnol.,* 16:250–258). Potential and actual uses of commercial electronic noses include food/beverage analysis, environmental monitoring, and medical diagnosis (Ping, W., Yi, T., Haibao, X., and Farong, S. (1997). *Biosens. Bioelectron.,* 12:1031–1036; Dickinson, T. A., White, J., Kauer, J. S., and Walt, D. R. (1998). *Trends Biotechnol.,* 16:250–258; Aathithan, S., Plant, J. C., Chaudry, A. N., and French, G. L. (2001). *J. Clin. Microbiol.,* 39:2590–2593).

Vapor phase chemical detection systems based on arrays of broadly-responsive sensors offer a number of potential advantages over traditional analytical devices. An electronic nose directly samples the air, so no sample preparation is necessary. The time required for detection is limited only by the time required for the chemical sensors to respond and for the pattern recognition calculation, which is fast using modern computer technology. With rapidly-responding sensors, rapid detection of volatiles is therefore possible. In addition, while traditional analytical instruments tend to be large and require considerable power, sensor array devices have the potential for being small and portable. Although handheld IMS devices are available, they are currently tuned to specific, restricted tasks, such as use of the Iontrack Instruments VaporTracer$^2$ for explosives or drugs, and therefore lack the broad-band nature of an electronic nose.

Sensor array devices also would also have a number of advantages over systems using mono-specific sensors. First, truly "mono-specific" sensors are difficult (if not impossible) to produce; broadly-responsive sensors can be readily made. Second, even if mono-specificity could be achieved, detection of several compounds would require development of a separate sensor for each compound of interest. Conversely, a relatively small array of broadly-responsive sensors is theoretically capable of discriminating a large number of different compounds (Alkasab, T. K., White, J., and Kauer, J. S. (2002). *Chem. Senses,* 27:261–275). Third, a device containing sensors specific for a finite number of compounds is incapable of detecting any others outside its defined target set. A device containing broadly-responsive sensors would have the potential for detecting and discriminating compounds of future interest.

It would be advantageous to develop sensors capable of detecting and correctly identifying a large range of volatile chemicals. Such sensors would be particularly useful in domestic security applications, such as detecting explosives and chemical warfare agents.

SUMMARY OF THE INVENTION

We have, surprisingly, discovered that nucleic acids with attached fluorophores and dried onto a substrate react with volatile chemical compounds in ambient air and can be used as sensors to detect compounds in the air that reacts thereto. This is distinctly different from other nucleic acid-based sensing materials that work only when both the analytes and nuclei acid materials are dissolved in aqueous solution.

Accordingly, the present invention provides a nucleic acid-based chemical sensor, sensing system and sensing and identification method which provide for a nucleic acid-based multi-sensor, cross-reactive, sensor array having a rapid response time, a rapid sampling time, dynamic modulation of sampling and detection parameters, intelligent feedback control of analyte sampling conditions, smart mode sampling, smart detection through application of sophisticated analyte detection algorithms, high throughput screening of sensors, and high sensitivity, discrimination, and detection capability for a variety of target analytes.

In one embodiment, the present invention provides a method for detecting a volatile compound in an air sample comprising the steps of:
 a) contacting said air sample with a nucleic acid-based sensor array comprising:
  i) a substrate; and
  ii) a nucleic acid attached to a fluorophore dispersed on the substrate, said nucleic acid attached to a fluorophore providing a characteristic optical response when subjected to excitation light energy in the presence of a volatile compound; and
 b) detecting the presence or absence of the volatile compound.
 c) identifying the volatile compound in the air sample.

The substrate can be fabricated of different materials, including, for example, papers, fiberglass, silk, and fabrics made of synthetic materials.

In a preferred embodiment, the nucleic acid/fluorophore is dispersed on a plurality of internal and external surfaces within the substrate.

In one embodiment, contacting is accomplished by drawing an air sample believed to contain the compound into a sample chamber and exposing the array to the air sample. In a preferred embodiment, the air sample is drawn through the chamber for no more than five seconds.

The detecting may be accomplished by illuminating said sensor with excitation light energy and measuring an optical response produced by the sensor due to the presence of said volatile compound with a detector means. Detector means include, for example, a variety of photodetectors such as photomultiplier tubes (PMTs), charge-coupled display device (CCD) detectors, photovoltaic devices, phototransistors, and photodiodes. In a preferred embodiment, filtered photodiode detectors are used.

In all embodiments, the volatile compound can be identified by employing a pattern-matching algorithm and comparing the optical response of the nucleic acid-based sensor array with the characteristic optical response.

In specific embodiments, the volatile compound can be identified by measuring the spatio-temporal response patterns of the optical response and recognizing the patterns through a method selected from template matching, neural networks, delay line neural networks, or statistical analysis. The air sample may be suspected of containing volatile compounds from a variety of substances, including explosive materials or chemical weapons agents.

The present invention further provides a sensing system for detecting and identifying a volatile compound in an ambient air sample. The system includes:
 a) a nucleic acid-based sensor array comprising a plurality of nucleic acids;
 b) a fluorophore attached to the nucleic acids;
 c) a plurality of substrates wherein the nucleic acids with fluorophore are attached to;
 d) a substrate support;
 e) an excitation light source array including a plurality of light sources optically coupled to the sensor elements;
 f) a detector array comprising a plurality of detectors optically coupled to said sensor elements;
 g) a sample chamber for housing the sensor elements, the light source array, and the detector array;
 h) a sampling means attached to the chamber for drawing the ambient air into the chamber for contact with the sensor array for a controlled exposure time;
 i) a controller means in electrical communication with the light sources, the detectors, and the sampling means, the controller means electrically coordinating and switching the sampling means with the light sources and the detectors for sampling the ambient air, measuring optical responses of the array sensors to the ambient air sample, and detecting the volatile compound; and
 j) an analyte identification algorithm for comparing the measured sensor optical responses to characteristic optical responses of the sensors to target analytes and identifying the analyte in the ambient air sample.

The sensing system may be in a hand-held device, attached to a shipping container, or used in conjunction with another screening device such as an x-ray screening machine. The sensing system may also be remotely controllable.

In a preferred embodiment the identification algorithm reports a detection event when the sensor responses are different from blank air and identifies the analyte present using a pattern-match algorithm as described above.

BRIEF DESCRIPTION OF THE DRAWINGS

This invention is pointed out with particularity in the appended claims. Other features and benefits of the present invention can be more clearly understood with reference to the specification and the accompanying drawings in which:

DETAILED DESCRIPTION OF THE INVENTION

The nucleic acid-based sensing method and sensing device design of the present invention mimics and parallels the structure and operational characteristics of the mammalian olfactory system through the combination of electro-optical hardware component modules, microprocessor control and software sampling and detection algorithms. The sample cavity design mimics the mammalian nasal cavity where odors (i.e. vapor analytes) are drawn into the sensing module ("sniffed" or "inhaled") and their interaction with a plurality of sensing elements ("sensory neurons") in a sensor array triggers an external event.

In one embodiment, analyte interaction with the nucleic acid/fluorophore-based sensing elements produces emitted light energy at a detectable characteristic wavelength when the sensor elements are illuminated by excitation light energy from a filtered LED array. The multi-element nucleic acid-based sensor array of the present invention thus mimics the sensory neurons of the olfactory system in responding to the external triggering event, emitted light energy signaling the presence of an analyte, and detecting this triggering event by way of a filtered photodiode array ("Detection"). The photodiode preamplifiers mimic an olfactory sensory neuron by converting the optical signal to an electrical voltage signal ("Transduction") which is amplified, manipulated and transported via electrical circuits ("Transmission") to an analog-digital ("A/D") converter and a software controlled microprocessor for data manipulation, analysis, feedback control, detection and identification ("Integration"). The Detection, Transduction, Transmission, and A/D features are replicated for each nucleic acid-based sensor element in the array. The sensor array of the present invention may be expanded or contracted without limit by adding or removing elements and channels according to the requisite analyte detection, discrimination and identification needs of a specific sampling application.

Figure 1:
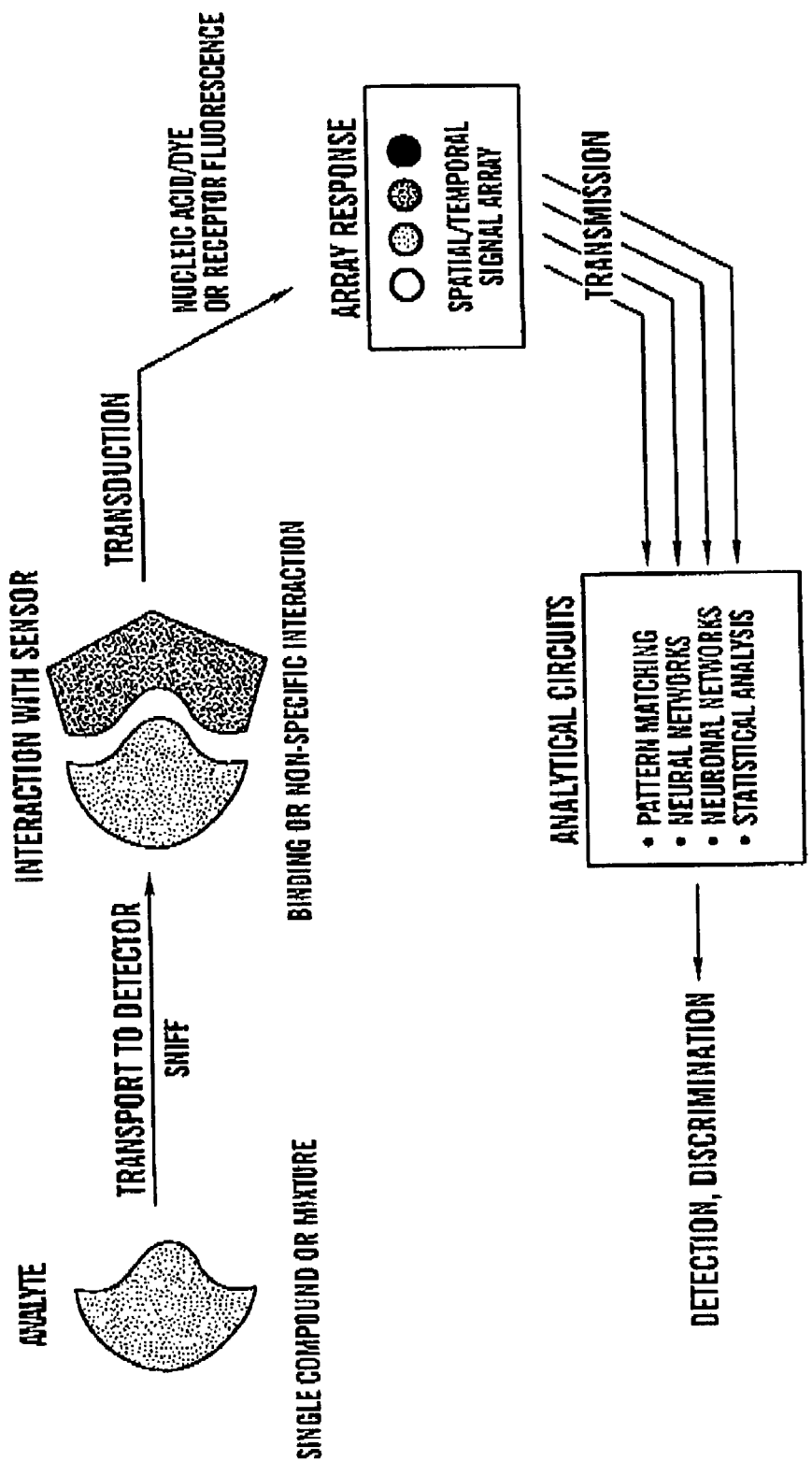
FIG. 1 is a schematic diagram of the analyte detection method of the present invention.

FIG. 1 provides an overview of the analyte sensing and detection method of the present invention. Ambient odors (analytes) are sniffed (transported to the sensor array) where the odors interact with the array of nucleic acid/fluorophore—based sensor elements. Light energy excitation of the sensor elements in the presence of the odors produces a detectable optical response signal due to changes in emitted light produced by analyte interaction with the nucleic acid/fluorophore compounds in the sensor elements. The spatiotemporal optical response of the nucleic acid-based array to the odor is detected, recorded, manipulated, and then matched to known target odors via smart analytical algorithms which apply, for example, pattern matching, neural network, neuronal network, or statistical analysis methods to detect, discriminate and identify the odor.

The hardware and software components and configuration of the nucleic acid/fluorophore-based sensor of the present invention provide for a compact, portable, inexpensive, expandable, rapidly responding sensing device that can modify its detection strategy on the fly. The design and method provides for real-time, on-the-fly, modulation of: a) the output of light emitting diodes (LEDs), such as wavelength, intensity, and frequency; b) the detection properties of photodiodes, such as wavelength, gain, and frequency; c) the sampling parameters, such as frequency, duration, number, velocity, and rise-fall dynamics; and d) sampling time constant or temporal filter settings, for dynamically responsive, smart feedback control in sampling, detection and identification of analytes.

In addition to dynamic response modulation, the device and method further provide for hardware and algorithm implementations which evaluate the synchrony and noise characteristics across different sensors, especially those of the same composition being examined at different wavelengths. This provides a powerful tool for identifying and utilizing small response signals and rejecting noise.

By providing for independently illuminated, detected, recorded, and modulated sensing channels, levels of flexibility, expandability, portability, efficiency, and economy are achieved that are difficult to realize with other sensor designs, light sources, filtering systems, and light detectors. In addition, the use of small, inexpensive, flexibly programmable, computational microcomputer platforms and interchangeable nucleic acid/fluorophore-based sensors and sensor array modules provide for extreme flexibility and tailoring of sensor performance and capabilities to real world sensing applications.

Nucleic acids useful according to the present invention include single and double-stranded RNA and single and double-stranded DNA and cDNA, also modified nucleic acids can be used. Nucleic acid, oligonucleotide, and similar terms used herein also include nucleic acid analogs, i.e. analogs having other than a phosphodiester backbone. For example, the so-called peptide nucleic acids, which are known in the art and have peptide bonds instead of phosphodiester bonds in the backbone are considered within the scope of the present invention (Nielsen et al. Science 254, 1497 (1991)). Alternatively, modified bases can be used in the nucleic acid sequence. Examples of such modified bases are listed below:

| Code | Modified base |
| --- | --- |
| ac4c | 4-acetylcytidine chm5u 5-(carboxyhydroxymethyl)uridine |
| cm | 2'-O-methylcytidine cm5u 5-carbamoylmethyluridine |
| cmnm | 5s2u 5-carboxymethylaminomethyl-2-thiouridine |
| cmnm | 5u 5-carboxymethylaminomethyluridine |
| d | dihydrouridine |
| fm | 2'-O-methylpseudouridine |
| gal | q beta,D-galactosylqueuosine |
| gm | 2'-O-methylguanosine |
| i | inosine |
| i6a | N6-isopentenyladenosine |
| m1a | 1-methyladenosine |
| m1am | 2'-O-methyl-1-methyladenosine |
| m1f | 1-methylpseudouridine |
| m1g | 1 -methylguanosine |

-continued

| Code | Modified base |
|---|---|
| m1i | 1-methylinosine |
| m22g | 2,2-dimethylguanosine |
| m22gm | N2,N2,3'-trimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| mam5s2u | 5-methylaminomethyl-2-thiouridine |
| mam5u | 5-methylaminomethyluridine |
| man q | beta,D-mannosylqueuosine |
| mcm5s2u | 5-methoxycarbonylmethyl-2-thiouridine |
| mcm5u | 5-methoxycarbonylmethyluridine |
| mo5u | 5-methoxyuridine |
| ms2i6a | 2-methylthio-N6-isopentenyladenosine |
| ms2t6a | N-((9-beta-D-ribofuranosyl-2-methylthiopurin-6-yl)carbamoyl)threonine |
| mt6a | N-((9-beta-D-ribofuranosylpurine-6-yl)N-methyl-carbamoyl)threonine |
| mv | uridine-5-oxoacetic acid methylester |
| o5u | uridine-5-oxyacetic acid(v) |
| osyw | wybutoxosine |
| p | pseudouridine |
| q | queuosine |
| s2c | 2-thiocytidine |
| s2t | 5-methyl-2-thiouridine |
| s2u | 2-thiouridine |
| s4u | 4-thiouridine |
| t | 5-methyluridine |
| t6a | N-((9-beta-D-ribofuranosylpurine-6-yl)carbamoyl)threonine |
| tm | 2'-O-methyl-5-methyluridine |
| um | 2'-O-methyluridine × 3-(3-amino-3-carboxypropyl)uridine,(acp3)U |
| yw | wybutosine |

The length of the nucleic acid sequences can vary between about 15 bases of single stranded DNA up to about 3 thousand base pairs of double stranded DNA. Preferably about 18–24 base pair oligonucleotides are used.

Nucleic acids useful according to the present invention can be synthesized using methods well known to one skilled in the art. For example, a solid-phase phosphotriester approach can be used as described in Sproat et al. (Solid-phase synthesis of oligodeoxyribonucleotides by the phosphotriester method, in Oligonucleotide Synthesis—A practical approach (Gait, M. J., Ed.), IRL Press, Oxford pp. 83–115, 1984). The concept of the solid-phase phosphotriester approach has four basic aspects: the oligonucleotide is synthesized while attached covalently to a solid support, excess soluble protected nucleotides and coupling reagent can drive a reaction near to completion, the reaction is carried out in a single reaction vessel to diminish mechanical losses due to solid support manipulation, allowing synthesis with minute quantities of starting materials, and the heterogeneous reactions are standardized. All these procedures are easily automated and several commercially available oligonucleotide synthesizers are known to one skilled in the art. The most used chemical route for solid-phase oligonucleotide synthesis is the phosphite triester method as modified by Beaucage and Caruthers (Beaucage, S. L., and Caruthers, M. H. (1981). Deoxynucleoside phosphoramidites—A new class of key intermediates for deoxypolynucleotide synthesis, Tetrahedron Lett. 22, 1859–1862).

Alternatively, nucleic acids can be isolated from libraries comprising nucleic acid fragments in the form of, for example, plasmids, cosmids, yeast artificial chromosomes, and bacterial artificial chromosomes. The nucleic acids can also be isolated from any other source such as viruses, and procaryotic or eucaryotic cells. Nucleic acid isolation methods are routine and protocols can be found, for example from Molecular Cloning: A Laboratory Manual, 3rd Ed., Sambrook and Russel, Cold Spring Harbor Laboratory Press, 2001.

After isolation, the isolated nucleic acids can be further modified, for example, by restriction enzyme digestion. Isolated nucleic acids can also be amplified using PCR and either random or specific primer sequences. Such primer sequences can also be labeled with a fluorophore during the oligonucleotide synthesis.

In one embodiment, the nucleic acids useful in the present invention are similar to aptamers which can be selected from existing aptamers or from random sequence libraries. Aptamers are defined as single-stranded or double-stranded nucleic acids which are capable of binding proteins or other small molecules with high specificity in aqueous solution. In the present invention, the nucleic acid-based sensors differ from aptamers in two important respects: 1) the nucleic acids sensors are dried onto a substrate and interact directly with compounds in the air, and 2) the nucleic acid sequences are selected for their capacity to react, in combination with a fluorophore, to broad ranges of volatile compounds. Generally, aptamers are selected from a large number of non-interacting oligonucleotides and they originate from in vitro selection experiments termed "SELEX" for systematic evolution of ligands by exponential enrichment, that, starting from random sequence libraries, optimize the nucleic acids for high-affinity binding to given ligands (C. Tuerk and L. Gold, Science 249, 505 (1990); A. D. Ellington and J. W. Szostak, Nature 346, 818 (1990)). Reviews on in vitro selection and aptamers, see, e.g., G. F. Joyce, Curr. Opin. Struct. Biol. 4, 331 (1994); L. Gold, B. Polisky, O. C. Uhlenbeck, M. Yarus, Annu. Rev. Biochem. 64, 763 (1995); J. R. Lorsch and J. W. Szostak, Acc. Chem. Res. 29, 103 (1996); T. Pan, Curr. Opin. Chem. Biol. 1, 17 (1997); Y. Li and R. R. Breaker, Curr. Opin. Struct. Biol. 9, 315 (1999); M. Famulok, Curr. Opin. Struct. Biol. 9, 324 (1999).

The length and nucleic acid sequence can be easily modified and thereby the repertoire of possible sensors is almost infinite.

To test the responsiveness of a nucleic acid to an odor, the isolated nucleic acids are consequently labeled with a fluorophore. As used herein the term "fluorophore" will be understood to refer to both fluorophores, phosphors and luminophores, and to chromophores that absorb but do not emit photons.

Fluorophores provide the means for transducing the interaction of the odorants with the sensor. For example, fluorophores useful according to the present invention include, but are not limited to OLIGREEN (Molecular Probes, Inc., Eugene, Oreg.), and other fluorescent dyes listed in the following Table 1.

| Fluorescent Dye | Excitation, nm | Emission, nm |
|---|---|---|
| 5-FAM | 494 | 518 |
| Alexa™ 488 | 495 | 520 |
| Alexa™ 532 | 531 | 554 |
| Alexa™ 546 | 555 | 570 |
| Alexa™ 555 | 555 | 565 |
| Alexa™ 568 | 579 | 604 |
| Alexa™ 594 | 590 | 615 |
| Alexa™ 647 | 649 | 666 |
| Alexa™ 647 | 649 | 666 |
| Alexa™ 660 | 663 | 690 |

-continued

| Fluorescent Dye | Excitation, nm | Emission, nm |
|---|---|---|
| Alexa ™ 660 | 663 | 690 |
| Allophycocyanin (APC) | 650 | 660 |
| Allophycocyanin (APC) | 650 | 660 |
| BODIPY ® 564/570 | 564 | 570 |
| BODIPY ® TMR | 542 | 574 |
| BODIPY ® 530/550 | 530 | 550 |
| BODIPY ® 558/568 | 558 | 568 |
| BODIPY ® 630-650 | 630 | 650 |
| BODIPY ® 630-650 | 630 | 650 |
| Calcein | 494 | 517 |
| Calcium Crimson ™ | 590 | 615 |
| Calcium Green ™ | 506 | 533 |
| Calcium Orange ™ | 549 | 576 |
| C-Phycocyanin | 620 | 648 |
| Cy2 ™ | 489 | 506 |
| Cy3.5 ™ | 581 | 596 |
| Cy3 ™ | 550 | 570 |
| Cy5.5 | 675 | 694 |
| Cy5.5 | 675 | 694 |
| Cy5 ™ | 649 | 670 |
| Cy5 ™ | 649 | 670 |
| DiD DilC(5) | 644 | 665 |
| DiD DilC(5) | 644 | 665 |
| dsRed | 558 | 583 |
| Ethidium Bromide | 518 | 605 |
| FAM | 488 | 508 |
| FITC | 494 | 518 |
| FluorX ™ | 494 | 519 |
| GFP | 488 | 558 |
| GFP Red Shifted (rsGFP) | 488 | 507 |
| JOE | 522 | 555 |
| JOE-514 | 514 | 549 |
| Magnesium Green ™ | 506 | 531 |
| Magnesium Orange ™ | 550 | 575 |
| Nile Red | 549 | 599 |
| Oregon Green ™ 488 | 496 | 524 |
| Oregon Green ™ 500 | 503 | 522 |
| PBXL-1 | 545 | 666 |
| PBXL-3 | 614 | 662 |
| Phycoerythrin, R & B | 565 | 575 |
| Pyronin Y | 555 | 580 |
| Red Reflect | 633 | 633 |
| Red Reflect | 633 | 633 |
| Rhodamine 110 | 496 | 520 |
| Rhodamine 123 | 507 | 529 |
| Rhodamine B | 555 | 580 |
| Rhodamine Green ™ | 502 | 527 |
| Rhodamine Phalloidin | 542 | 565 |
| Rhodamine Red ™ | 570 | 590 |
| RiboGreen ™ | 500 | 525 |
| ROX | 580 | 605 |
| R-phycocyanin | 618 | 642 |
| R-Phycoerythrin (R-PE) | 565 | 575 |
| SYBR Green | 497 | 520 |
| Sypro Ruby | 450 | 610 |
| TAMRA | 555 | 575 |
| Thiadicarbocyanine | 651 | 671 |
| Thiadicarbocyanine | 651 | 671 |
| TO-PRO ™-1 | 514 | 533 |
| TO-PRO ™-3 | 642 | 660 |
| TO-PRO ™-3 | 642 | 660 |
| YO-PRO ™-1 | 491 | 509 |
| YO-PRO ™-3 | 612 | 631 |
| YOYO ™-3 | 612 | 631 |

Preferred dyes include OLIGREEN or YO-PRO dye (Molecular Probes, Inc., Eugene, Oreg.).

In addition to labeling each oligomer with a single type of fluorophore, fluorophore/quencher systems can also be used. Typically, these systems incorporate a fluorophore (e.g., fluorescein) and a quencher (e.g., DABCYL) at the ends of an oligomer sequence that forms a hairpin structure (see, e.g., Tyagi, S. and Kramer, F. R. (1996). Nature Biotech., 14:303–308; Hamaguchi, N., Ellington, A., and Stanton, M. (2001). Anal. Biochem., 294:126–131). In this conformation, the DABCYL quenches the fluorescein fluorescence through fluorescence resonance energy transfer (FRET). Upon binding of the oligomer sequence to its target ligand, the conformation of the oligomer changes, separating the fluorophore and quencher. This separation decreases the FRET between the fluorophore and quencher, causing a change in fluorescence at the fluorophore emission wavelength.

These energy transfer pairs for fluorophore/quencher systems where both the donor and acceptor are covalently bound to the same nucleic acid are known to one skilled in the art. Such energy transfer pairs have been used to detect changes in oligonucleotide conformation, such as in Tyagi et al. (EP 0 745 690 A2 (1996)) and Pitner et al. (U.S. Pat. No. 5,691,145 (1997)). They also have been used to detect cleavage of the oligonucleotide at a point between the donor and acceptor dyes, such as in Han et al. (U.S. Pat. No. 5,763,181 (1998)), Nadeau et al. (U.S. Pat. No. 5,846,726 (1998)), and Wang et al. (ANTIVIRAL CHEMISTRY & CHEMOTHERAPY 8, 303 (1997)). Energy transfer pairs covalently bound to oligonucleotides have also been used to provide a shift in the ultimate emission wavelength upon excitation of the donor dye, such as by Ju (U.S. Pat. No. 5,804,386 (1998)).

Other fluorophore/quencher systems have been described in the art and such systems can be used according to the present invention. For example, the combination of a non-covalently bound nucleic acid stain with a covalently attached fluorophore on a single-stranded oligonucleotide hybridization probe has been used to detect specific DNA target sequences by monitoring the fluorescence of either the nucleic acid stain or the covalent label, such as described in Lee and Fuerst (PCT Int. Appl. WO 99 28,500). Also, U.S. Pat. No. 6,333,327 discloses fluorophore/quencher systems for decreasing background fluorescence during amplification assays and in ligation assays, and for detecting hybridization.

Nucleic acids in the nucleic acid-based sensors of the present invention are labeled using techniques known to one skilled in the art. Such methods include, for example, mixing the nucleic acids with a dye, end-labeling the nucleic acids during oligonucleotide synthesis, or labeling the nucleic acids during a PCR reaction.

Application of dyes can be performed in various ways. Dyes, such as for example OLIGREEN and TOTO family of cyanine dimer dyes (Molecular Probes, Inc.) can be applied directly onto the nucleic acids to produce a labeled nucleic acid.

Nucleic acids can also be labeled directly during their synthesis. Reagents are readily available (e.g., Glen Research, Sterling, Va.) for adding fluorescent dye molecules to the 3' and 5' ends, as well as labeled dT for inserting the dye molecule within the nucleic acid sequence. Use of direct labeling allows control over the precise amount and location of the fluorophore within the nucleic acid sequence. Also, a fluorophore may be added at different locations or multiple fluorophores at several locations in the nucleic acid sequence which allows development of even greater variety of sensors.

The sequence and/or structure of the nucleic acid used to construct a sensors, effects the response profile of the sensor. In preparing the nucleic acid-based sensors, the effect of sequence (and, hence, structure) on the response properties of nucleic acid-based sensors is tested. For each sequence tested, the folding structure(s) and melting temperature(s) are determined to determine the effect of a specific DNA structure on the odorant responses.

Figure 11:
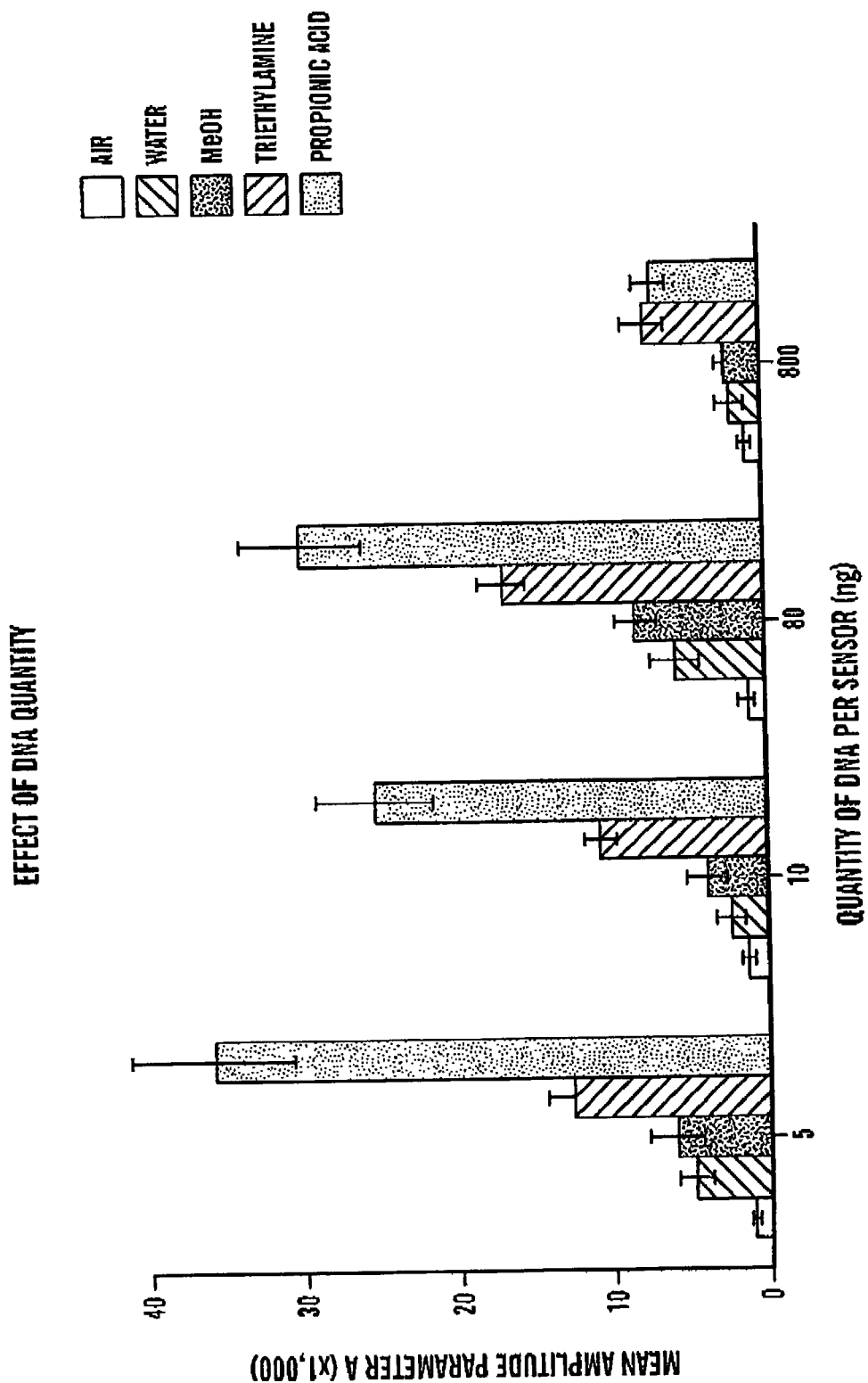
FIG. 11 shows responses of sensors made from YO-PRO and increasing quantities of pBluescript DNA applied to a sensor substrate. Each bar represents the mean of 10 replicates, error bases indicate±S.D.

The amount of nucleic acids used in producing the nucleic acid-based sensor effects the response of the sensor to a volatile compound. For example, effects of DNA quantity were seen in preliminary experiments on the nucleic acid based sensors (FIG. 11). Therefore, for each sensor configuration, a range of nucleic acid and dye concentrations (for applied dyes) are tested for the amount that produces the desired result, i.e. a clearly noticeable response to a test odor.

It is desirable to apply the nucleic acid/fluorophore solution to the substrate as evenly as possible. For example, an inkjet application system can be used. With this system, a piezo-electric inkjet ejects 50 nl droplets of solution, which are applied to the substrate in precise locations using an XYZ positioning system. The inkjet system can be used to apply nucleic acid/fluorophore solutions to the sensor substrates.

The substrate used to make the sensor can be fabricated from different materials, such as, for example, silk, papers, fiberglass, fabrics made of synthetic materials.

Long-term stability of the nucleic acid/fluorophore-based sensor responses is important for their use in the present invention. Fluorescent dyes can photobleach upon repeated exposure to excitation light, and different dyes photobleach at different rates. The present invention is designed to minimize photobleaching (by limiting light exposure to brief 1 msec pulses), and the odorant recognition algorithms are resistant to changes in signal amplitude. Reducing any possible photobleaching, however, will increase the life expectancy of the sensor.

Dried nucleic acids are usually stable for long periods of time which makes it an ideal sensor material. However, it is possible that the nucleic acid used in the odorant sensors degrades over time thereby altering odorant response. The degradation is likely to be minimal and can be easily tested. Odorant responses over repeated sniffs are compared to the data from, for example the photobleaching tests described above. Any signal decrease that cannot be accounted for by photobleaching will suggest a nucleic acid degradation effect. If evidence of nucleic acid degradation is found, nucleotide modifications that reduce nuclease degradation can be used to reduce degradation as described, e.g., for applications to aptamers (see Jayasena, S. D. (1999). *Clin. Chem.*, 45:1628–1650).

The present invention provides nucleic acid/fluorophore-based array sensor element compositions disposed on substrates which may be either inert or active during analyte sampling and detection. While inert supports are typically used in conventional sensing devices, the present invention provides for active dye support materials that enhance sensor responses to specific analytes by their unique chemical, physical, adsorption, or optical characteristics. Different substrate support materials may be employed within a single array where specific support materials are matched to specific fluorophores, fluorophore compounds and nucleic acid/fluorophore mixtures to produce enhanced sensor responses to specific volatile analytes or odors.

Fibrous substrate supports, which enhance sensor response signals for a variety of fluorophores and nucleic acid/fluorophore mixtures are preferred substrate materials.

An additional advantageous feature of the present invention is in providing for removable or interchangeable nucleic acid/fluorophore-based arrays, array substrates, or substrate supports to facilitate changing sensor arrays to match specific analyte sampling and detection requirements. In one embodiment, multiple layers of array substrates may be employed for diversification and enhancement of sensor detection capabilities for identifying both broad and specific classes of analytes.

One skilled in the art would recognize that it is generally preferred to position sensor substrates at the appropriate viewing angle and distance from light emitting diode excitation light sources and photodiode detectors so as to provide for optimum sensor signal generation and detection. In one preferred embodiment, a separate substrate holder may be provided for positioning and securing array substrates. In an alternative preferred embodiment, the sample chamber housing may be configured for proper positioning and securing array substrate.

As will be appreciated by those in the art, the number of possible substrate materials is very large. Possible substrate materials include, but are not limited to, silk, glass and modified or functionalized glass, plastics (including acrylics, polystyrene and copolymers of styrene and other materials, polypropylene, polyethylene, polybutylene, polyurethanes, teflons, etc.), polysaccharides, nylon or nitrocellulose, resins, silica or silica-based materials including silicon and modified silicon, carbon, metals, inorganic glasses, plastics, and a variety of other polymers.

In preferred embodiments, optically transparent substrates are employed to permit placement of the substrate between LED light sources and photodiode detectors as shown in FIG. 3. In alternative embodiments, where the LEDs and photodiodes are placed on the same side of the substrate, optically opaque or optically absorbing, reflective, and scattering materials may be employed.

Where conventional flat, planar, curved or non-planar solid sensor substrates are used, these substrates are generally self-supporting and substrate supports are not required but may be optionally employed.

While conventional flat, planar, or curved non-planar solid sensor substrates may be employed, increased sensor surface area can arise from depositing dyes on highly convoluted surfaces that include fine fibrous hairs of different materials, particulates, porous substrates, or films and substrates suspended within the sampling stream. With the innovative substrates of the present invention, these preferred substrate embodiments provide enhanced contact and interaction between sample target analytes and sensor elements, increased optical response signal per unit of sensor geometrical surface area, and increased optical response signal per unit of sensor volume.

In preferred embodiments, highly permeable, high surface area, textured, fibrous or particulate substrates which have substantial open porosity for unimpeded transport of vapors and fluids are desired. In preferred embodiments, single or multi-ply layers of papers, felts, laid, or woven fibrous materials or fabrics are employed. In alternative embodiments, loosely packed individual fibrous or particulate materials may be employed.

In a most preferred embodiment, fibrous substrate materials are employed for signal enhancement. Important considerations in selecting fibrous substrates are substrate permeability to vapors, high accessible surface area per unit volume, response signal enhancement for specific analytes, how the substrate interacts with the sample flow to provide open access of its external and internal surfaces to analytes for interaction with the sensing material. While particularly useful fiber substrates are porous, lightweight paper or tissue products, for example Kimwipe™ (Kimberly-Clark Corp., Roswell, Ga.), lens papers, facial tissues, and products made from cotton, rayon, glass, and nitrocellulose fibers, other fibrous materials employing natural or synthetic fibers such as felt, batting, textiles, woven fabrics, yarns, threads, string, rope, papers, and laminates or composites of such materials would be equally suitable as long as they possess the requisite fluid permeability, surface area, surface area to volume ratio, and open porosity for free transport of vapor and fluid analytes.

Particularly useful inorganic fibers and fibrous material compositions are natural and synthetic fibers made from glass, ceramic, metal, quartz, silica, silicon, silicate, silicide, silicon carbide, silicon nitride, alumina, aluminate, aluminide, carbon, graphite, boron, borate, boride, and boron nitride. Particularly useful natural or synthetic fibers and fibrous material compositions are polymer fibers made from aromatic polyamides, nylons, polyarylonitrile, polyesters, olefins, acrylics, cellulose, acetates, anidex, aramids, azlon, alatoesters, lyocell, spandex, melamines, modacrylic, nitrile, polybenzimidazole, polyproplylene, rayons, lyorell, sarans, vinyon, triacetate, vinyl, rayon, carbon pitch, epoxies, silicones, sol gels, polyphenylene-benzobis-ozazole, polyphenylene sulfides, polytetrafluoroethylene, teflon, and low density or high density polyethylene. In one preferred embodiment, fiber materials that are highly absorbent and have good dye retention characteristics, for example the cellulosic fiber known as Lyorell, may be employed.

In alternative embodiments, fibers may be coated with either chemical sizing, polymer, ceramic or metallic materials. Chemical sizing such as modified polyvinyl acetates, organosilanes, coupling agents, anti-static agents and lubricants may be employed as appropriate.

With respect to signal enhancing sensor substrate properties of the present invention, one skilled in the art would generally recognize and understand the intended meaning of the term "textured" generally referring to material surfaces which typically have a distribution of surface topographical features, such as high points (peaks) and low points (valleys), ranging from +/−100 run to +/−1000 um RMS, the term "high permeability" generally referring to materials and material structures with a high open porosity that provide essentially free, unimpeded access and convective or diffusive transport to low viscosity fluids, the term "high surface area" generally referring to materials that have a surface area of at least 1 $M^2/g$ and typically refers to surface areas ranging between 2 to 500 $M^2/g$, the term "high surface area to volume" generally referring to materials having a surface area to volume ratio of at least 1 $M^2/cm^3$ and typically refers to surface area to volume rations ranging between 2 to 1000 $1M^2/cm^3$, the terms "porous" or "porosity" generally referring to materials having a distribution of pore sizes ranging from 100 nm to 1000 μm, and the term "high open porosity" generally referring to materials whose pore distributions substantially comprise open pores.

In alternative embodiments, the sensor substrates of the present invention may be chemically or physically modified to enhance surface area, absorption, adhesion, hydrophobicity, hydrophilicity, repulsion, discrimination or specificity. In some embodiments, the substrate may be chemically altered to provide chemical functionality for interaction with analytes, such as providing for enhanced affinity, enhanced repulsion, or steric impediments to analyte adsorption.

In a preferred embodiment, the sensors are made on a substrate of acid-washed silkscreen, preferably about 16xx and sized about 10 mm×12 mm. The nucleic acid/fluorophore mixture is pipetted onto a silkscreen, preferably about 5–50 μl of nucleic acid/fluorophore mixture is used, and allowed to air dry for about 10–60 minutes, preferably about 20–30 minutes, most preferably about 25 minutes. Each sensor is rinsed in 70% ethanol for about 5 minutes, allowed to air dry, then attached to supports on, for example, glass coverslips.

The nucleic acid/fluorophore-based sensor and sensing system of the present invention provides for a rapidly responding, relatively inexpensive, dynamically configurable, intelligent, portable artificial sampling device.

The device delivers analytes (odors) in a controlled, pulsatile manner (sniff) to nucleic acid/fluorophore—based sensor array and detector array system that generates signals, for example, analog electrical signals. The number of sensors, detectors, and sampling time points can be made larger or smaller depending on the classes of analytes that are being targeted for detection. Analog signals, for example, are amplified and filtered by a pre-amplifier/amplifier module and digitized by an analog/digital conversion module for storage in a computer memory module. All attributes of the sensing process, including odor delivery, sampling, analysis, detection and identification are under programmable software control via a computer.

The sensing device housing the nucleic acid/fluorophore-based array is easily trained to recognize specific analytes. Training consists of delivering a known set of analytes, for example DNT and other nitroaromatic compounds for detection of explosives, to the device, one analyte at a time, and storing matrices of values that are a spatio-temporal signatures of each analyte in memory. When an unknown analyte is to be sampled after training, it is delivered to the device and a matrix of values acquired from the unknown is compared to matrix templates for the variety of analytes stored in memory during the training phase. The best match between the unknown and the library of stored matrices is then determined using a number of different algorithms. In one embodiment, the algorithm looks for the best match after calculating the sum of the squared differences between each point in the stored and unknown matrices. In a preferred embodiment, the rising phase of each sensor signal is fit by an exponential function containing two parameters describing the signal amplitude and rate of change. A matrix of these parameters is then used to represent the sensor array response, and matches are calculated as above using sum of squared differences.

The sensing system provides output results in a variety formats including, but not limited to screen displays, plots, printouts, database files, and recorded or synthesized voice messages.

The sensing device of the present invention comprises a sampling chamber housing an analyte delivery system and a multi-channel array comprising light emitting diodes (LEDs) focused through an array of excitation filters onto individual sensor elements of a sensor array. An array of photodiodes, filtered with an array of emission filters, detects emitted light energy produced by illuminating the sensor elements with LED excitation light during interaction with analytes that are drawn into the sample chamber by the analyte delivery system. The ambient temperature, humidity, and particulate levels in the sample chamber may be controlled for improved reproducibility in sampling under a variety of environmental conditions.

The changes in emitted light detected by the photodiode array for each sensor element are digitized by either 12 bit or, alternatively, 20 bit analogue-to-digital converters and stored in a computer memory module. Analyte sampling, detection, and identification are controlled by a programmable microcontroller directed by smart sampling and detection algorithms. The device provides for fast, high gain, low noise, real-time sampling, detection and identification of a variety of vapor analytes with high sensitivity and low detection limits, typically in the sub ppm to ppb concentration range. The device further provides for intelligent sampling and detection through real-time, dynamic modulation of sampling conditions and detection criteria with real-time feedback control for optimizing device sensitivity, discrimination, and detection of a variety of analytes.

The sensing device of the present invention provides for generating optimized signals for different dye/nucleic acid combinations by using different excitation and emission wavelengths for different sensor types. Unlike conventional sensing devices, with the present invention, this can be achieved simultaneously while sampling the entire array of sensing elements in parallel using an array of individual LED-sensor-photodiode sensing channels operating at appropriate wavelengths for a variety of sensor-analyte combinations.

The sensing device generally provides the basic function comprising analyte delivery and control (i.e. manipulation of spatial and temporal distributions; control over temperature, humidity, and duty cycle), detection by a sensor array and transduction of sensor signals into a manipulatable format, analysis of transduction output events, and dynamic feedback control over analyte delivery, detection and analysis for intelligent sampling and detection and optimization of nucleic acid/fluorophore-based sensor sensitivity and analyte discrimination.

Figure 2:
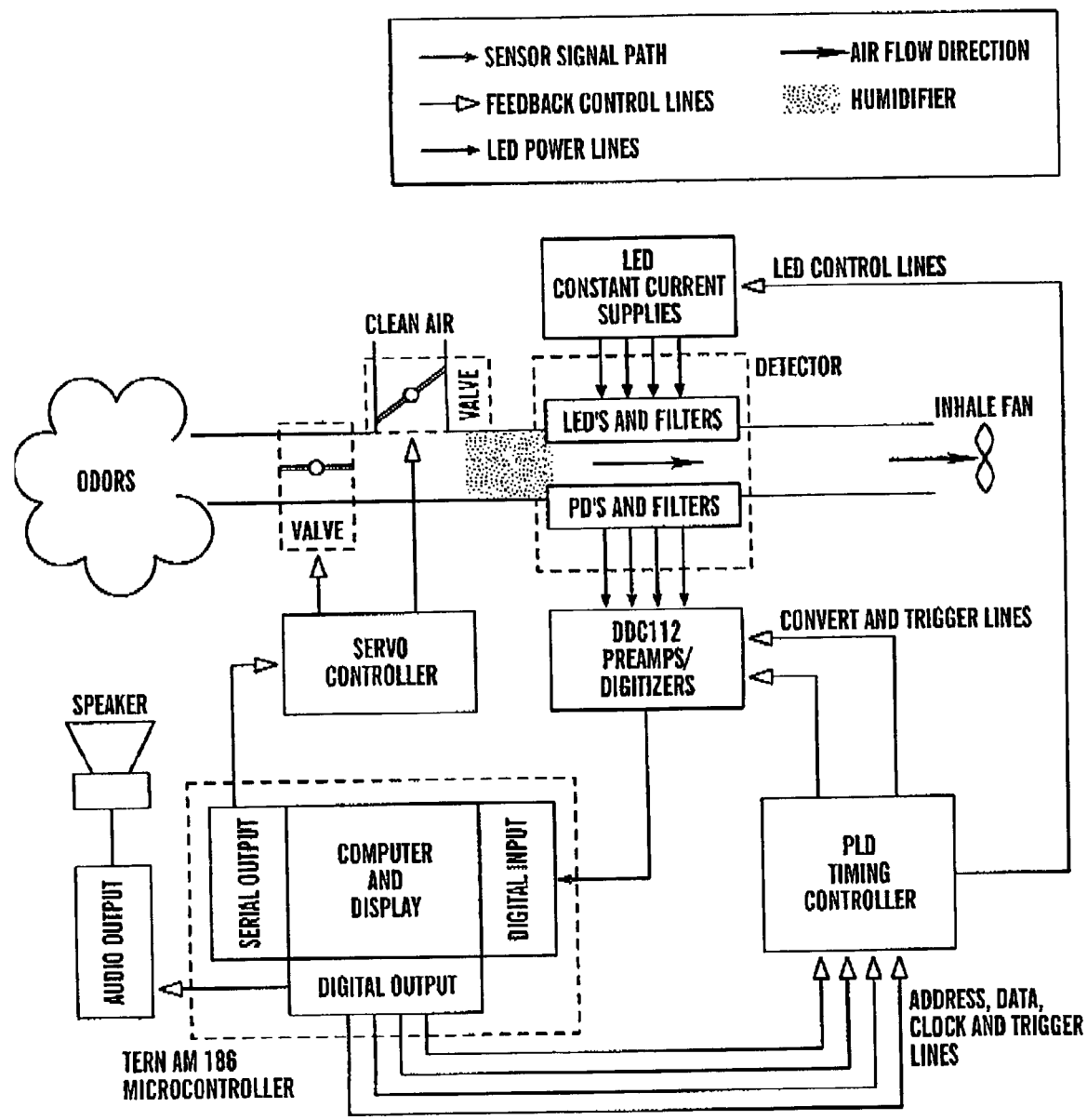
FIG. 2 is a block diagram showing hardware components of the sensing system of the present invention.
Figure 3A:
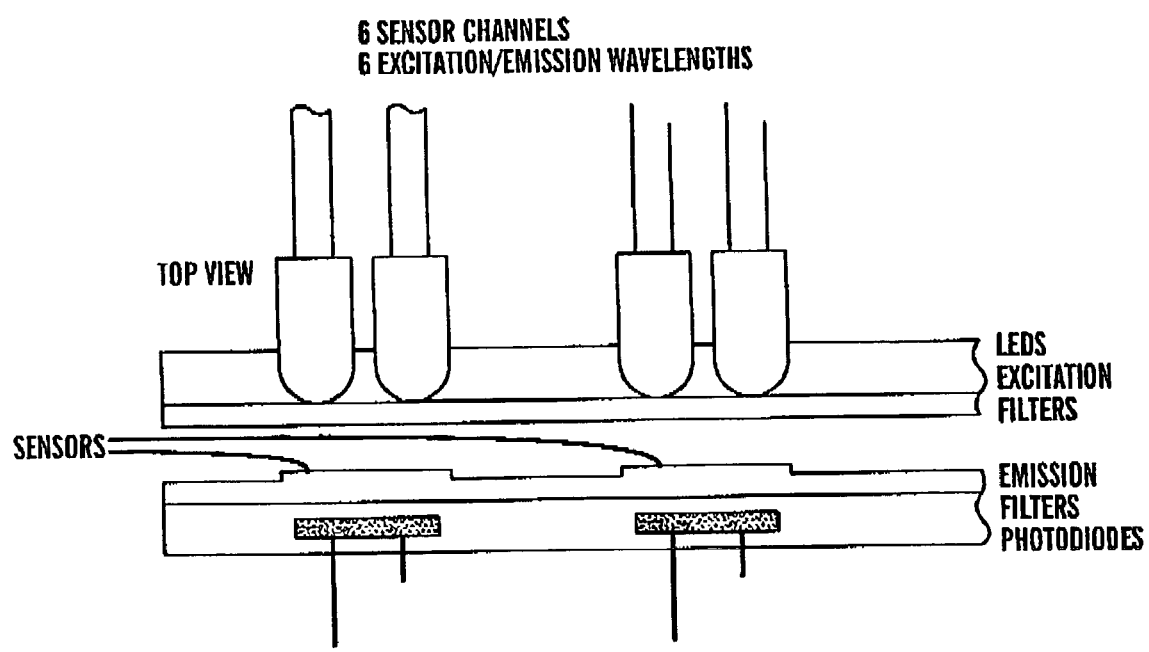
FIGS. 3A–3B show a schematic diagram of a sample detection chamber of the present invention.
Figure 3B:
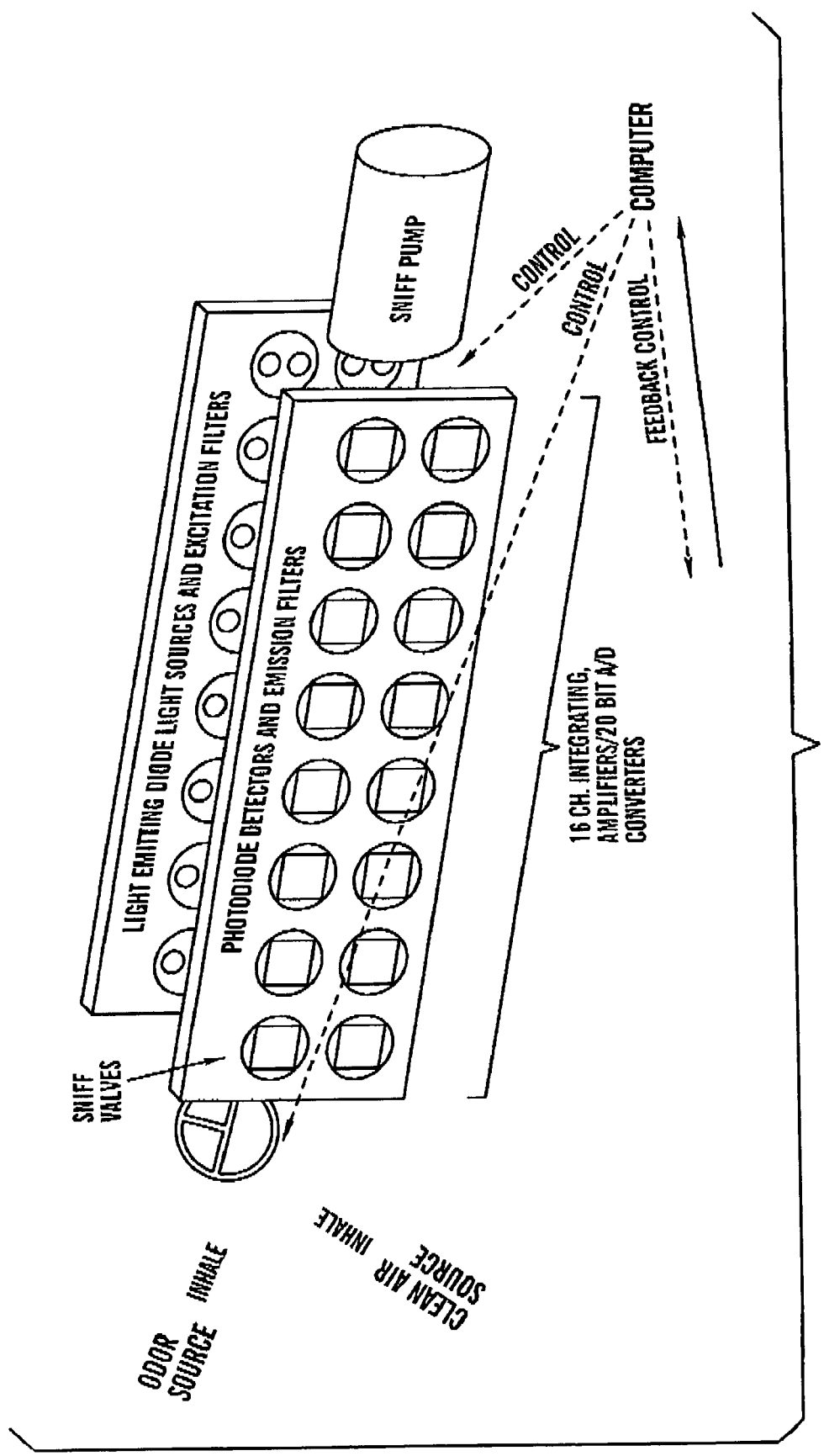

FIG. 2 provides a schematic block diagram showing the general modular design and configuration of the preferred nucleic acid/fluorophore-based sensor array and sensing system components. A detailed schematic of an exemplary sensor array configuration showing LEDs, excitation filters, sensor elements, emission filters, and photodiodes is provided in FIG. 3A FIG. 3B provides an exemplary schematic showing the position of a valve controlling air flow from the odor source and clean air, 16 channels of integrating amplifiers and 20 bit A/D converters, light emitting diode light sources and excitation filters and photodiode and emission filters as well as the position of a pump which is used to sniff the air sample into the system.

For reliable and reproducible sampling of air, it is important to standardize sampling and sensing conditions by controlling the delivery and presentation of analytes to the sensor array. In a preferred embodiment, the analyte delivery system provides feedback control over sample temperature, humidity, flowrate, and the rise and fall times, duration, and frequency of analyte delivery.

One embodiment of the analyte delivery system is shown in FIGS. 2 and 3. Generally the sensing chamber consists of a tube through which the analyte vapor passes. The sensing array with opposed light emitting diode light sources and photodiode photodetectors with sensor elements is placed within a sample chamber. In this configuration the incoming air stream generated by a gated negative pressure (i.e. a sniff pump such as a fan, pump, 'mesopump', bellows, or their equivalents) causes the air sample to be drawn into the sensing chamber and to be expelled to the ambient environment by the negative pressure source. In this manner, analyte vapor pulses are delivered to the sensing array from ambient pressure sources. The sensing chamber can be of the form of a simple tube, as described above, or may assume any shape that may improve or optimize the delivery of the analyte pulse to the sensor array, including complex shapes modeled after the structure of the nasal cavity of animals. In one embodiment, complex cavities with multiple baffles are used to prevent ambient light and ambient air movements from interfering with the generation of standardized pulses of analyte to the sensor array.

Generally, the sensing chamber includes: a) a means for controlling temperature, humidity, air flowrate, rise and fall times and frequency of the applied vapor pulses; b) a means for controlling the surface properties of the sensing and non-sensing areas of the chamber (liquid, mucus, or gel lining) in order to impart chromatographic surfaces to the sensing area and/or humidify, dehumidify, or distribute the analyte to the sensory surface, or to optimize response of the sensing chemistry; c) a means for aerodynamic control over chamber shape which may either be held constant for the duration of analyte delivery or modulated by feedback control during analyte delivery; and d) a means for active, dynamic feedback control over shape, duration, air flowrate, temporal envelope, and frequency of analyte sampling (sniffing). Such feedback may be derived from examining the spatio-temporal response patterns from the sensor array produced by prior analyte sampling.

A cross-sectional view of a sampling chamber embodiment showing detection sites is provided in FIGS. 3A and 3B. In designing the sampling chamber, it is necessary to configure the chamber, sensors, LEDs and photodiodes to comply with focal length dimensions of the integral lenses that are incorporated into the LEDs and photodiodes. Focal lengths of the integral lenses were measured and, based on these dimensions, the width of the sample chamber and the positions of the sensors within the sample chamber were arranged such that the sensors were optimally illuminated by the LEDs and optimally observed by the photodiodes at their respective appropriate focal distances.

The present invention provides for control over the sensing chamber environment where, for example, ambient light levels, aerodynamic flow conditions, sample humidity and temperature can be measured, standardized, controlled, adjusted, or modulated for different analyte detection tasks.

The sensing chamber can be optimized for its aerodynamic properties by placing the detectors in cavities of various shapes. In one embodiment, the sensors may be placed at a bend in the flow path. In an alternative embodiment, the sensors may be located on the side of the straight flow path. In a preferred embodiment, the sensor is attached to an inclining ramp in the flow path of a straight chamber. Since the device is unique in its use of ambient air flow sniffing and dynamic information gathering, it provides an opportunity to exploit the aerodynamic properties of complex spaces for improved sampling performance. For example, the chamber space may be configured to mimic the actual shape of the mammalian nasal cavity, or, alternatively, it may be configured to provide preferred fluid flow or aerodynamic design features. These embodiments would complement the design capability of the present invention which provides for static and dynamic control and modulation of inhalation and exhalation during sampling.

In one embodiment, humidification of the chamber and analyte sample is achieved by humidifying the incoming (inhalation) air stream in the entry nozzle prior to passing over the sensor array. In one method, humidification is accomplished by placing an absorbent material, such as filter paper, within the air tubing. The absorbent surfaces are connected by wicks to vials of water, thereby keeping them moist. In alternative embodiments, the humidity of the source may also be modulated by spraying water mist on the sampling area before sniffing. This will frequently increase the volatility of odors and improve detectability. While other humidification methods may be employed, the primary objective is to provide a means for balancing the humidity levels of the ambient air sample with those of the analyte source. In a preferred embodiment, precise control of humidity in the chamber could be accomplished by using specific chamber sensors to detect humidity levels which supply feedback to a moisture metering system.

The vapor sampling method of the present device is inspired by the sniffing behavior of animals. Odors are presented in a pulsatile fashion ("sniffs") to the sensor array through a fan and valve arrangement. In one embodiment, there are two fans and associated valves to control bi-directional, inhalation and exhalation air flows. In a preferred embodiment (FIG. 2), there is a single fan (for example, an Ametek 3" blower, 12 VDC, part no. 119349-01) drawing air through a 5 cm diameter tube about 1.5 m long, that is attached to the sensor head. The tube can also act as a handle for positioning the sensor head and as a vacuum buffer to reduce the effects of fluctuations in flow produced by the fan. Air flow is preferably maintained in a constant direction over the sensors. During sampling, the flow is switched to an odor inlet directed toward the ground. Between odor samples, clean air is drawn through a snorkel directed away from the ground to clear the sensors.

Valves are positioned by servos, which are controlled by the microprocessor through serial communication with a servo controller (for example, Mini SSC II, Scott Edwards Electronics, Inc.). Using the high vacuum blower (for example Ametek), sniff samples, preferably about 1 sec sniff samples are taken to obtain a relatively small volume of air (for example, about 450 cc).

In one embodiment, a simple, "straight-through" sensor chamber configuration is used. This configuration allows for flexibility, ease of construction, and simplified aerodynamics. In a preferred embodiment, however, the airstream is partially obstructed by elevating the sensing substrates. Such configuration enhances signal size, by increasing the exposure of the sensing surface to the air flow.

As discussed elsewhere, sensing elements are composed of nucleic acid/fluorophore mixtures applied to removable sensor substrates. In one embodiment, thin films of nucleic acid/fluorophore mixture are deposited on a flat silk, plastic or glass substrate. In preferred embodiments, a nucleic acid/fluorophore mixture is deposited directly onto fibrous support made from silk, natural or synthetic cellulose, polymers, glasses, ceramics, metallic, or other materials using an ink jet printer. The use of fibrous dye substrates dramatically increases the magnitude of the response signals, which improves analyte detection and discrimination of the device. In an alternative embodiment, thin nucleic acid/fluorophore films can be suspended freely across a perforated removable solid support which is placed in the center of the air flow stream, thereby exposing both sides of the nucleic acid sensor to volatile compound analyte.

The sensing device according to the present invention uses interchangeable, removable sensors or sensor elements comprising a support wherein nucleic acid/fluorophore complexes are attached. Easily removable sensors facilitate rapidly changing sensing sites for improving the sensitivity and optimizing discrimination for specific analytes in a variety of sampling applications. This feature further provides for rapid screening of different nucleic acid/fluorophore mixtures for evaluating new nucleic acid sequences and or structures or different fluorophores for use in sensors and also for evaluating analytical detection algorithms.

The size, thickness and surface area of sensor element sites may be modified to optimize sensitivity and discrimination and to efficiently couple sensor elements to light sources and detectors. Generally, a larger sensor geometric area and a close matching of the sensor element geometric area with photodetector area will provide better sensitivity.

The cross-reactive sensor array of the present invention may comprise either narrow or broadly responsive sensor elements. The number of sensor array elements can be configured for specific sampling application requirements. Specific sensors for defined analytical tasks can be chosen from among the many possible sensing element sites present in the array. Sensor and array configurations may be modified through the addition of LED-sensor-photodiode-filter channels depending on the requirements of a particular analyte discrimination task.

In one preferred embodiment, multiple sensor arrays and array substrates may be deployed in the sampling chamber. Such multiple arrays may comprise a series of hierarchically organized sensor arrays such that the first interaction and sampling of the analyte is with a broadly responsive sensor array and, subsequently, the analyte sample is automatically diverted for additional sniffs, on the basis of analytical information fed back from the computer, to specific second order arrays designed to detect and identify the specific type of analyte. Thus, a plurality of sensing arrays may be arranged hierarchically so that ever finer discriminations can take place successively along the pathway. Additionally, the longevity of sensors can be extended by redundant arrays that are protected from exposure until needed, by delivery of analytes as short pulses, and by reducing light exposure by rapidly pulsing LEDs. To further reduce light exposure, low light excitation levels can be used if high sensitivity photodetectors such as avalanche photodiodes are employed. Rapid short pulsing of analytes prevents sensing surfaces from saturating, thereby improving sensor recovery following analyte exposure.

For enhanced, smart mode operation, the number of array sensors used in sampling or detecting an analyte may be modified, in real-time during either actual sampling or post-sampling data analysis using "on-the-fly" intelligent feedback control. By way of example, if a specific sensor is unresponsive to a particular analyte sample, the corresponding sensing channel may be automatically removed from consideration by a smart sampling or analysis algorithm which provides feedback control to the microcontroller. In addition, the weighting of individual sensors in the analysis and detection algorithm may be adjusted based on the signal contribution of individual sensors. Given that individual sensors have different breadths and peaks of response, sensor weighting will vary for different analytes.

In one preferred embodiment a 16 or 32 channel sensor array is employed. For example, it is anticipated that an optimized array of thirty-two sensor elements should have the capability of detecting and discriminating at least 1000 different analyte types. Because the nucleic acid/fluorophore-based sensor materials employed provide almost infinite diversity in their variety and therefore their analyte detection capability and can be selected to have appropriately broad spectra of response, different optimized sensor arrays can be selected for particular analyte detection tasks. While the results presented in the following Example were generated with an array size of 16 sensor elements, one skilled in the art may increase or decrease both the size of the sensor array and number of sensing channels, following the teachings disclosed herein, for meeting specific sensing application requirements.

Typically, epi-illuminating optics are employed in conventional fluorescence sensing systems. Epi-illuminating optics require relatively complex dichroic mirror arrangements for each channel where a different excitation and emission wavelength is used. Thus, in the epi-illumination format an excitation filter, a dichroic mirror, and an emission filter are required for each wavelength. The sensing system of the present invention employs a trans-illumination configuration where only excitation and emission filters are needed. Since the epi-illumination mode typically requires critical optical component alignment and is sensitive to vibration and movement, the trans-illumination mode of the present invention is advantageous for robust, compact, portable sensing devices for field sampling of ambient environments.

A schematic diagram of the optical detection system of the present invention is provided in the block diagram of FIG. 2. FIG. 3A provides a cross-sectional view of the sampling chamber that schematically shows the configuration and relative orientation of individual LED-photodiodes-optical filters-sensor sets within the sampling chamber housing. For simplicity, the cross-sectional view in FIG. 3A shows only two sensing channels, comprising two LED-photodiode-filter-sensor channel pairings. FIG. 3b shows a view of a sixteen sensor array configuration. It is important to note that the partial array configurations shown in FIGS. 3A and 3B are merely used to demonstrate, by way of example, the relative orientation and positioning of the sensors, filters, photodiodes and LEDs in the sampling chamber and are not intended to indicate any limitation in the size of sensor arrays that may be employed in the present invention. The actual sensing device of the present invention may employ larger or smaller arrays and any number of sensing channels with corresponding LED-photodiode-filter-sensor sets. For example, in one preferred embodiment, 32 LED-photodiode-optical filters-sensor channel sets are employed. The number of sensor array channels may be increased or decreased depending on specific sampling applications and analyte discrimination requirements.

Figure 4A:
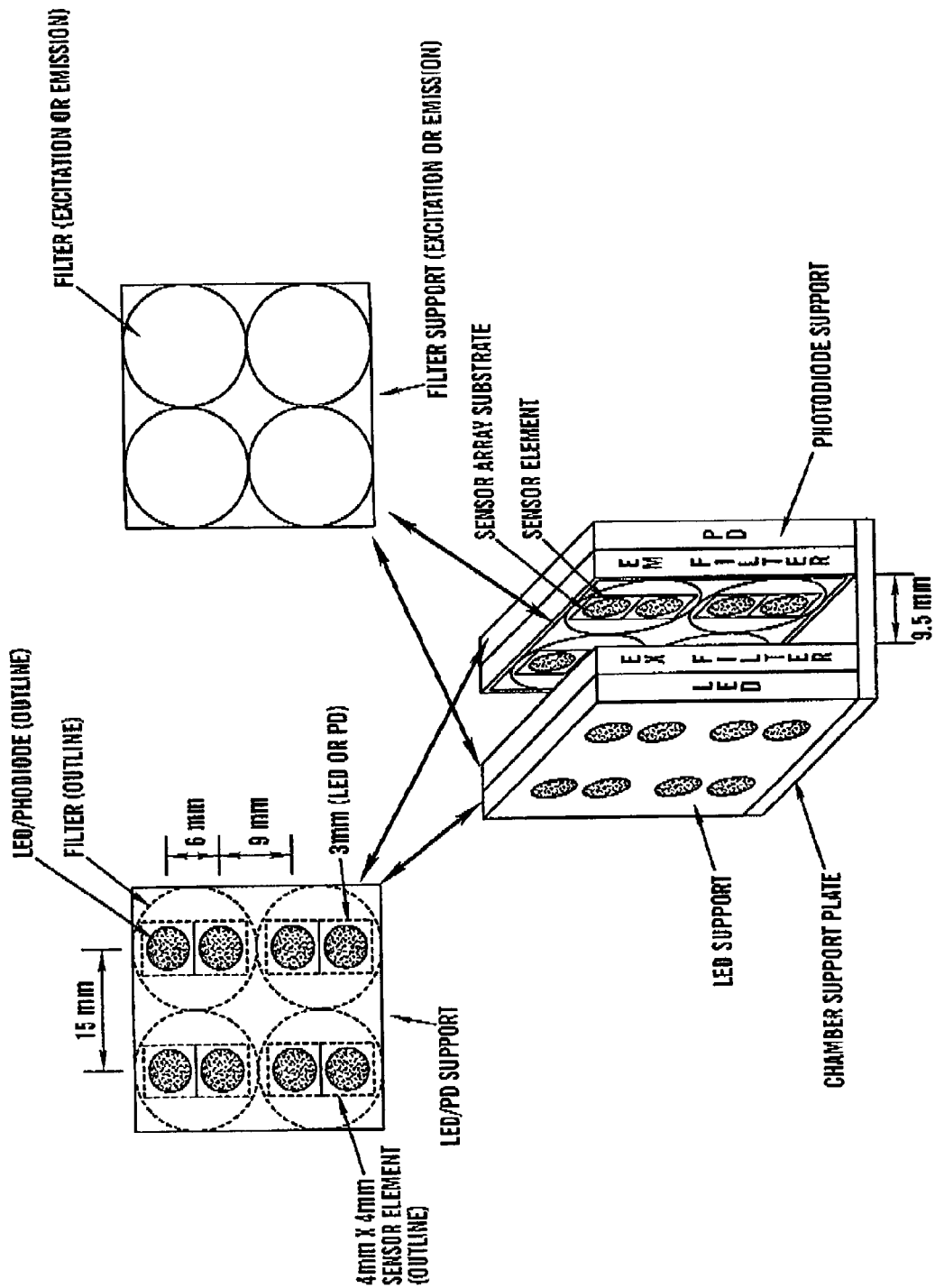
FIGS. 4A–4B are schematic diagrams showing a typical sensor array module configuration for the sensor of the present invention.
Figure 4B:
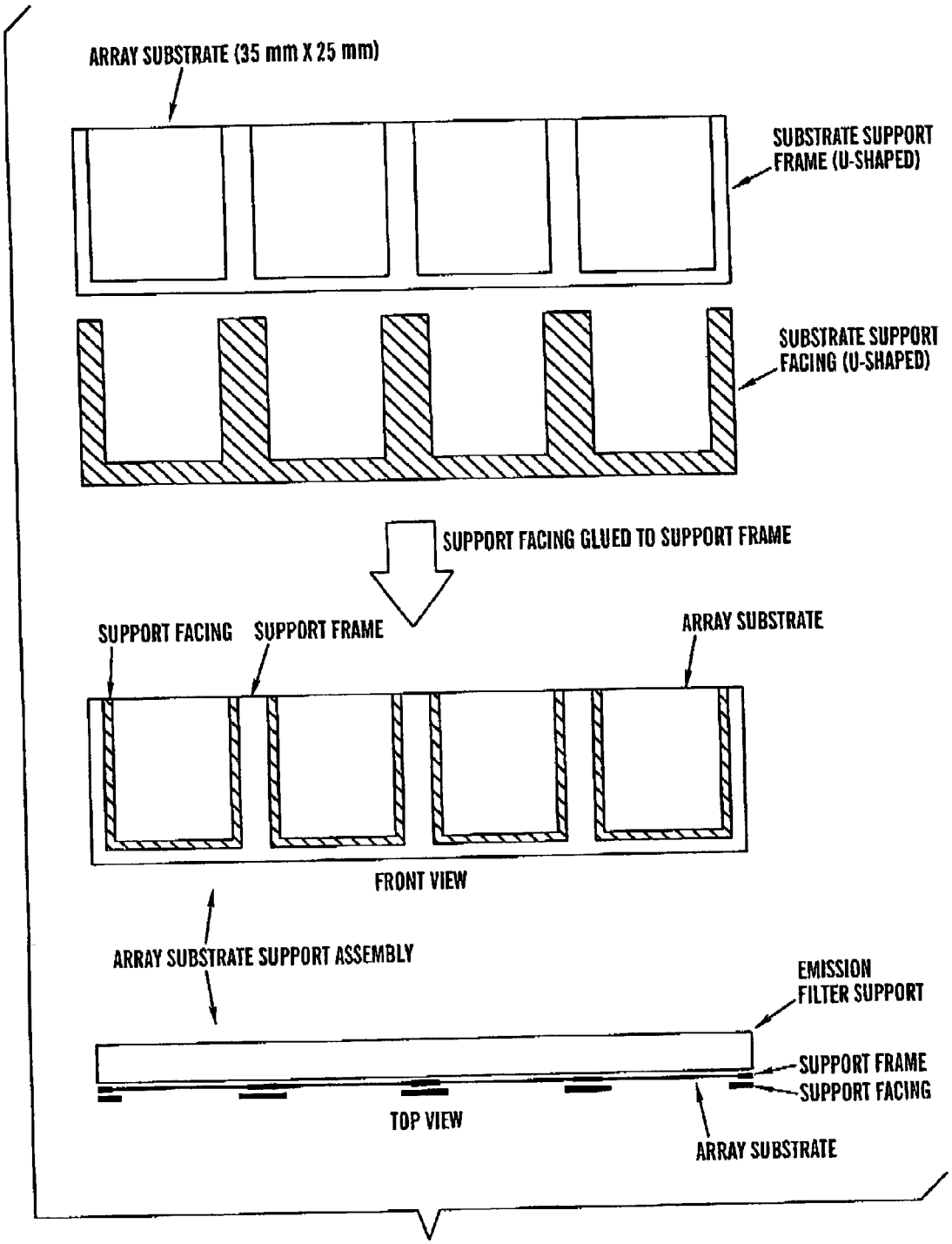

An example of the configuration and relative orientation of LEDs, photodiodes, excitation filters and emission filters, sensors and sensor array substrate is shown schematically in FIGS. 4A and 4B. While an eight sensor-LED-photodiode-filter module is shown in FIG. 4A by way of example, larger and smaller modules and arrays may be constructed based on specific sampling and detection needs. For example, in one embodiment, a 32 element sensor array may be assembled from four modules aligned side-by-side with eight sensors in each module. As shown in FIG. 4A, a plurality of LEDs are mounted on a nominally 30 mm×30 mm×6 mm black plastic support by drilling two columns of four 3 mm holes in a 2×4 array configuration. The LEDs are press fit into the mounting holes and may be readily removed for replacement. A photodiode support with the same dimensions is used for mounting a plurality of eight photodiodes in a 2×4 array configuration. Both the LED and photodiode arrays are mounted in columns with pair row spacings of 6 mm center to center and interpair spacings of 8 mm center to center. Column spacing for both the LED array and photodiode array is 15 mm center to center.

Figure 12A:
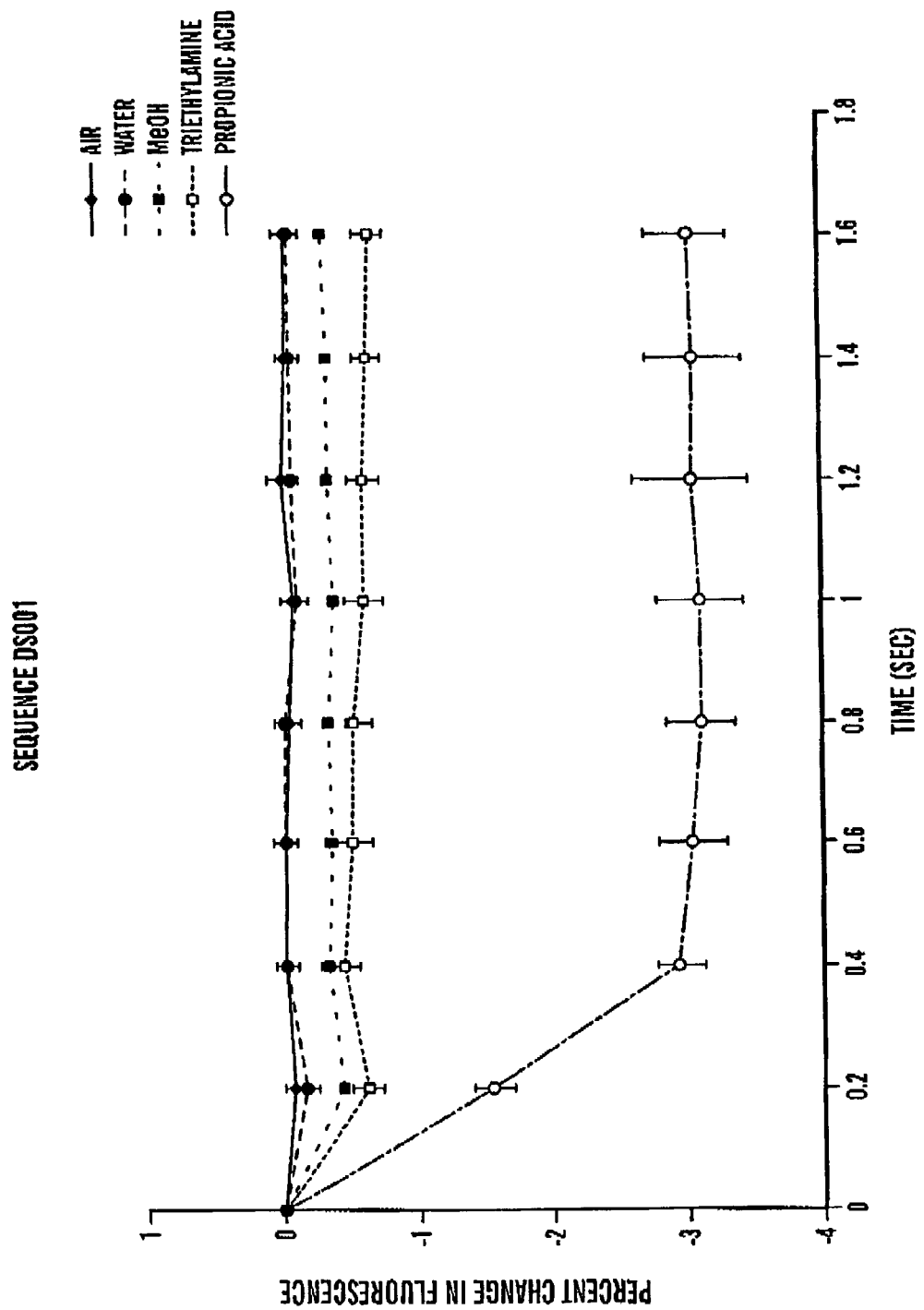
FIGS. 12A and 12B show responses of sensors made from short sequences of double-stranded DNA (DS001, FIG. 12A and DS002, FIG. 12B) and YO-PRO dye.
Figure 12B:
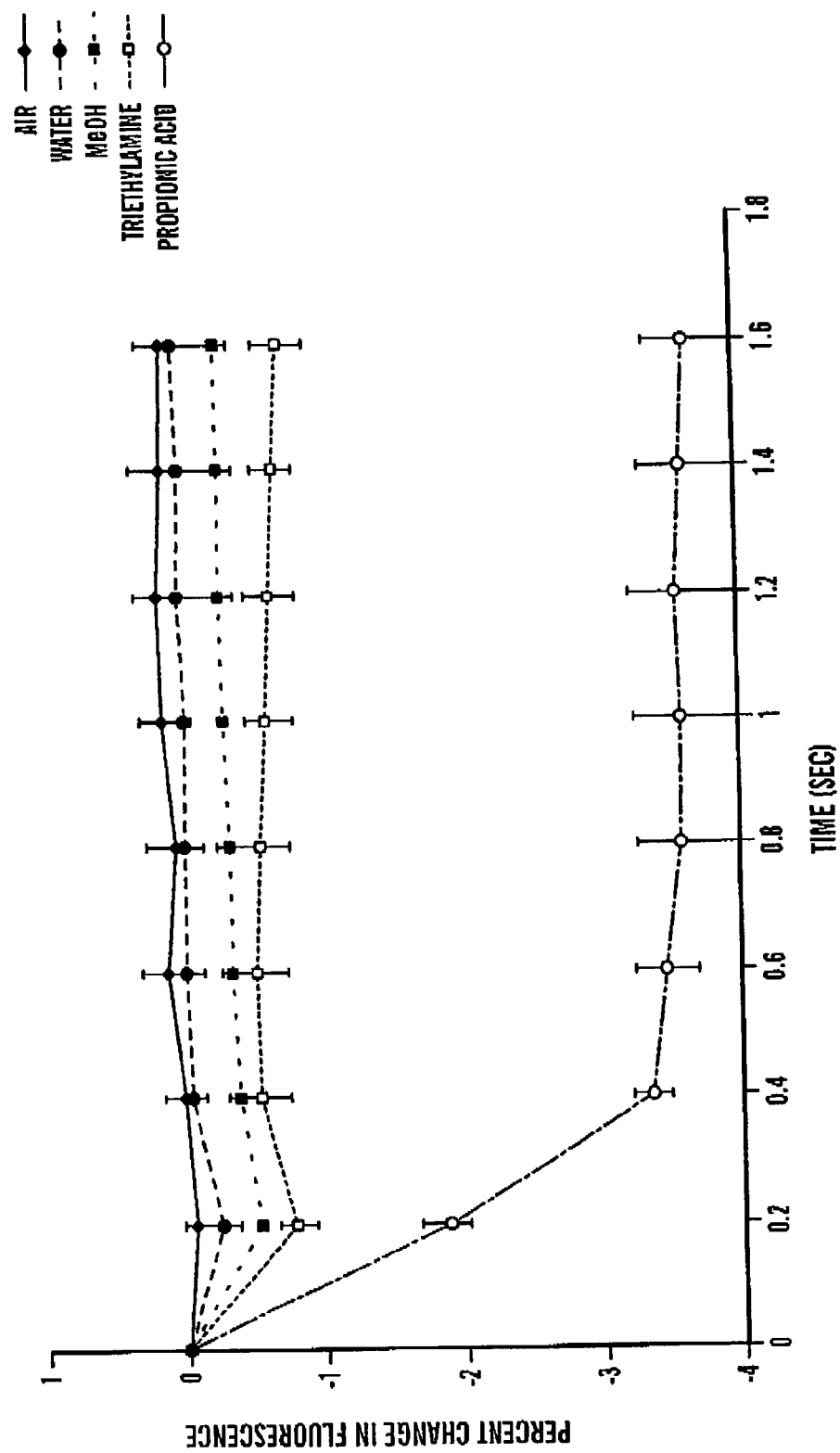

As shown in FIG. 4A, 12.5 mm (½") diameter excitation filters are mounted on an approximately 30 mm×30 mm×6 mm excitation filter support formed by drilling four ½" holes in a black plastic support plate to accommodate the filters in a 2×2 array configuration. Other filter assembly configurations, containing a larger or smaller filter array with larger or smaller filters may be employed in other embodiments. A similar emission filter support with the same dimensions as the excitation filter support is fabricated for mounting four emission filters. The emission filters and excitation filters are mounted to their respective supports with conventional set screws. The resulting excitation filter support assembly is attached directly to the front face of the LED support assembly and the emission filter support assembly is attached directly to the front face of the photodiode support assembly with conventional mounting screws.

A plurality of nucleic acid-based sensor elements are applied either directly to a transparent sensor array substrate, for example a glass coverslip, as coatings or droplets. Alternatively, where porous or fibrous sensing elements are employed, these may be attached, for example, taped, glued, or clamped, to a transparent sensor array substrate, or suspended over openings or perforations in an array support which may be either transparent or opaque. As shown schematically in FIG. 4B, removable, interchangeable sensor array substrates, or array support substrates, are mounted flush with the front face of the emission filter support using an substrate support holder. The substrate support holder is formed by attaching, for example by gluing, a shaped, preferably U-shaped substrate support frame and a shaped substrate support facing to the front fact of the emission filter support. The sensor array substrates, or array support substrates, are, for example mounted in a slot or channel formed by the substrate support frame, support facing and front face of the filter support as shown in FIG. 4B. The substrate support assembly provides for rapid removal and replacement of the interchangeable array substrates or array support substrates.

The sensor array may comprise either a single sensor array module, as shown in FIG. 4A, or a plurality of sensor modules aligned edge-to-edge to form a multi-module array containing a large number of sensor elements. The bottom edge of both the LED-excitation filter module support assembly and the photodiode-emission filter-sensor module support assembly are secured to a chamber support plate with conventional mounting screws. In this configuration, the excitation filter side of the LED assembly faces the sensor array side of the photodiode assembly. The LED and photodiode modules, or plurality of modules, are preferably aligned parallel to one another with spacing between the two modules adjusted to optimize illumination of the sensor array elements by the LED array. In one preferred embodiment shown in FIG. 4A, this spacing is approximately 5 mm. In one preferred embodiment, a 32 sensor array is formed by mounting four eight sensor modules to the chamber support plate. Other configurations using larger or smaller sensor modules and a fewer or greater number of modules may be employed to accommodate smaller or larger arrays by adjusting the size of the LED, photodiode, filter and sensor supports and chamber support plate and adjusting the spacing between opposing LED and photodiode modules to optimize illumination of sensor array elements by the LED array.

Commercially available, optical bandpass excitation filters for LED light sources and emission filters for photodiode detectors were obtained from Andover Corp. (Salem, N.H.) and Coherent Inc. (Santa Clara, Calif.). While these filters are available in ¼ to 1½ inch sizes, ½ inch filters were used in the preferred embodiment. By way of example, FIG. 4A shows schematically the relative orientation, configuration and spacing of excitation and emission filters for an embodiment which employs 32 sensors and sensing channels. For simplicity, FIG. 4A shows only one of four eight-sensor modules employed in a 32 channel sensor array. In this embodiment, with four sensor modules, 16 excitation filters are arranged in a 2×8 array with a center to center distance of 15 mm. With this embodiment, each emission filter covers a pair of two adjacent photodiodes having a 6 mm center to center spacing. In this particular embodiment, the 32 sensor elements in the array were aligned with the center of the LED-photodiode pair sight line. Other embodiments are envisioned where each sensor channel has its own individual excitation and emission filter or where more than two sensor channels share each excitation and emission filter. For example, for YO-PRO and Oligreen dyes, an excitation filter of 450 nm with a 40 nm bandwidth, and emission filters with 550 nm with a 70 nm bandwidth can be used (Coherent Inc., Santa Clara, Calif.). Dyes such as BOBO-3 and Cy3 require longer wave lengths which one skilled in the art is capable of selecting.

Illumination of sensor elements with excitation light energy may be accomplished with any appropriate light source. Thus, filtered light emitting diodes (LEDs), solid state lasers, or incandescent light sources of the appropriate wavelengths for the dye indicators being used may be employed. In a preferred embodiment, each LED light is passed through an excitation filter matched to a specific sensor element dye excitation wavelength. Where excitation filters are employed, broad band ("white") LEDs with appropriate wavelength filters may be used.

Unlike other sensors, by providing individually filtered sensing channels, the present invention enables simultaneous sampling at multiple excitation wavelengths and multiple emission wavelengths with different sensor elements. The present invention uniquely provides for individual control over the amplitude, duration, and duty cycle of illumination for each sensing channel in the array. Control over noise is exerted by feedback. Control over response to ambient light and optimization of signal detection, including reduction of dye bleaching, is accomplished by switching and modulating LED output and coordinate amplifier detection at various frequencies, ranging from kilohertz to megahertz. Control over ambient light interference may be achieved by phase locked LED flashing and photodiode detection.

In the present invention, nucleic acid-based sensor elements are illuminated directly by focused, light emitting diodes (LEDs) of the correct wavelength for each sensor dye material. Other advantages achieved from using LED excitation light sources are low power requirements, cooler operating temperatures, and high light output over small area. Additionally, by employing LED light sources for each sensor channel, each LED channel can be rapidly and independently switched electrically without use of a mechanical shutter. The LED channels can be individually modulated electrically at high rates by feedback from the microcontroller. In addition, the LED channels can be individually filtered for presenting different excitation wavelengths in parallel, thereby avoiding serially and mechanically switching filters during array measurements.

The LEDs useful according to the present invention for the nucleic acid based sensors include, for example, Hosfelt #25–365, Ultra Bright Blue LED, rated at about 466 nm. Other LEDs useful according to the present invention can be selected according to wavelengths appropriate for each and every fluorescent molecule that can be attached to the nucleic acids as shown in the Table above.

The LED's are turned on and off under computer control. Since these devices can respond at high speeds, up to megahertz frequencies, they are typically flashed at kilohertz frequencies in order to reduce bleaching. Such switching speeds cannot be achieved using mechanical shutters. The rapid switching capacities of LED's are utilized to flash them on and off in order to reduce sensor bleaching during data acquisition, thereby reducing total light exposure by shortened duty cycle during sample sniffs. LEDs are rapidly flickered so that light is only on during the time when data are being taken and then turned off between data points and between trials.

While a variety of photodetectors such as photomultiplier tubes (PMTs), charge-coupled display device (CCD) detectors, photovoltaic devices, phototransistors, and photodiodes may be used for detecting sensor response signals, in a preferred embodiment, filtered photodiode detectors are employed. In another preferred embodiment, highly sensitive avalanche photodiodes may be employed. Photodiode detectors have distinct advantages compared to conventional CCD camera detectors since they enable independent control and modulation of individual channel optical filtering, current/voltage conversion, signal amplification, and temporal filtering. Other specific advantages are low power consumption, relatively simple electronic circuitry, high sensitivity, configurability, multiple array formats (e.g. circular, square, or linear arrays), fast high frequency response at megahertz frequencies, low noise, wide dynamic range, and use with low frequency circuits.

In the nucleic acid-based sensing device of the present invention, an array of filtered photodiodes is employed where each filtered photodiode is either aligned with one filtered LED or, alternatively, groups of filtered photodiodes may be illuminated by a single filtered LED. The individual photodiodes are each aligned with an individual sensor element site with an optical emission filter that is appropriate for the specific dye employed by the individual sensor. Different emission filters may be used for each photodiode or, alternatively, one emission filter may be shared by multiple photodiodes. Photodiode signal noise is controlled by feedback. Additionally, feedback control is exerted over the signal sampling duration and time course. Differential signal inputs may be employed with a separate control sensor and individual sampling sensors. In one preferred embodiment, highly sensitive avalanche photodiodes may be used to permit lower required LED intensity for sensor of excitation and for reducing detector noise.

In one embodiment commercially available EG&G VTP 1232 photodiodes (EG&G, Inc, Gaithersburg, Md.) and 12.5 mm emission filters (Andover Corp., Salem, N.H. and Coherent Inc., Santa Clara, Calif.) were used. In a preferred embodiment, large area photodiodes (Hamamatsu part no. S2387-66R) are used. Specific emission filters used in conjunction with the photodiode detectors are discussed above.

While sensors may share the same LED, photodiode and excitation/emission filters, in alternative embodiments, separate LED, photodiode, sensor, and excitation/emission filters may be employed for each of sensor element and sensing channel. In one embodiment, individual sensor elements and sensing channels may employ different sensing materials, different excitation wavelengths, and/or different emission wavelengths simultaneously. While the results provided in Example 1 were generated using a 16 sensor array, one skilled in the art may increase or decrease both the size of the sensor array and number of sensing channels, following the teachings disclosed herein.

In one embodiment, all LEDs are powered by a single constant voltage circuit. The changes in fluorescence as a result of the odor interacting with the sensing material is detected by a photodiode and current to voltage (I/V) converter originally designed by Warner Instruments (Hamden, Conn.) and now commercially available from Red Shirt Imaging Inc. (Fairfield, Conn.). There is one I/V converter and amplifier/filter for each detector channel. The unique feature of this converter/amplifier configuration is that when the LEDs are activated prior to sample delivery, the background fluorescence signal produced by the sensor elements may be offset by resetting the amplifiers to a baseline value so that a full range of high gain amplification may be used to observe small changes in the signals generated by analytes during sampling. In addition, the amplifier board has the option for software control to be exerted over the gain and the filter time constants for all the channels. Photodiode output is digitized using a 12 bit A/D converter. In a preferred embodiment, each LED is powered independently by its own constant current circuitry. The output current of each photodiode is converted to voltage and digitized to 20 bits using an integrating preamp/AD converter IC manufactured by Burr-Brown (DDC 112). The DDC112's provide separate gain control for each sensor channel. Circuitry containing two programmable logic devices (PLD; Xilinx part no. XC95108-15PC84C) generates the high speed timing control signals for the 16 DDC112 chips.

Thus, in addition to being able to manipulate the onset and duration of the illumination and of the sniff as described above, the time constants and gain of the amplifiers can also be controlled in real time during data acquisition. These hardware features offer distinct advantages for optimizing the response of the sensing device for detection, discrimination and identification of analytes or odors of interest.

Generally, the nucleic acid/fluorophore-based sensing system of the present invention analyzes spatial-temporal patterns of data output from nucleic acid-based sensor arrays in order to characterize and identify the delivered sample or its analyte components. Useable information from the sensing array is obtained from the pattern of sensor response activity generated by all sensor elements over time and is evaluated using statistical measures such as information theory. Pattern recognition algorithms including template comparison, neural networks, principal components analysis, etc. may be implemented either in conventional digital CPUs, in neuronal network simulator chips, or in analogue neuronal network computers. Additionally, algorithms based on biologically based neuronal connections from the olfactory system and other neuronal circuits in the brain may be employed.

The analytical circuits of the present sensing device provide the requisite hardware support for the detection, discrimination and identification capability of the sensing system.

The present invention uses temporal control over stimulus presentation and the examination of the resulting changes in sensor output over time. Unlike other designs, with the present invention analyte presentation to the sensing sites is carried out by negative pressure 'sniffing', rather than by positive pressure pulsing which requires samples to be enclosed in confined containers. Additionally, the present invention uses sniffing parameters that can be electronically modulated by feedback from via computer control and flow rate, sniff duration, and temporal profile can be adjusted and modulated for specific sampling environments and target analytes to detect ambient odors drawn into the sensing chamber. Sampling modulations can be carried out in real time so that subsequent sniffs can be modified by the preceding ones. With the smart sampling mode capability of the present invention, a computer turns the sniff on and off and can modulate and control sniff parameters during sampling.

Figure 6:
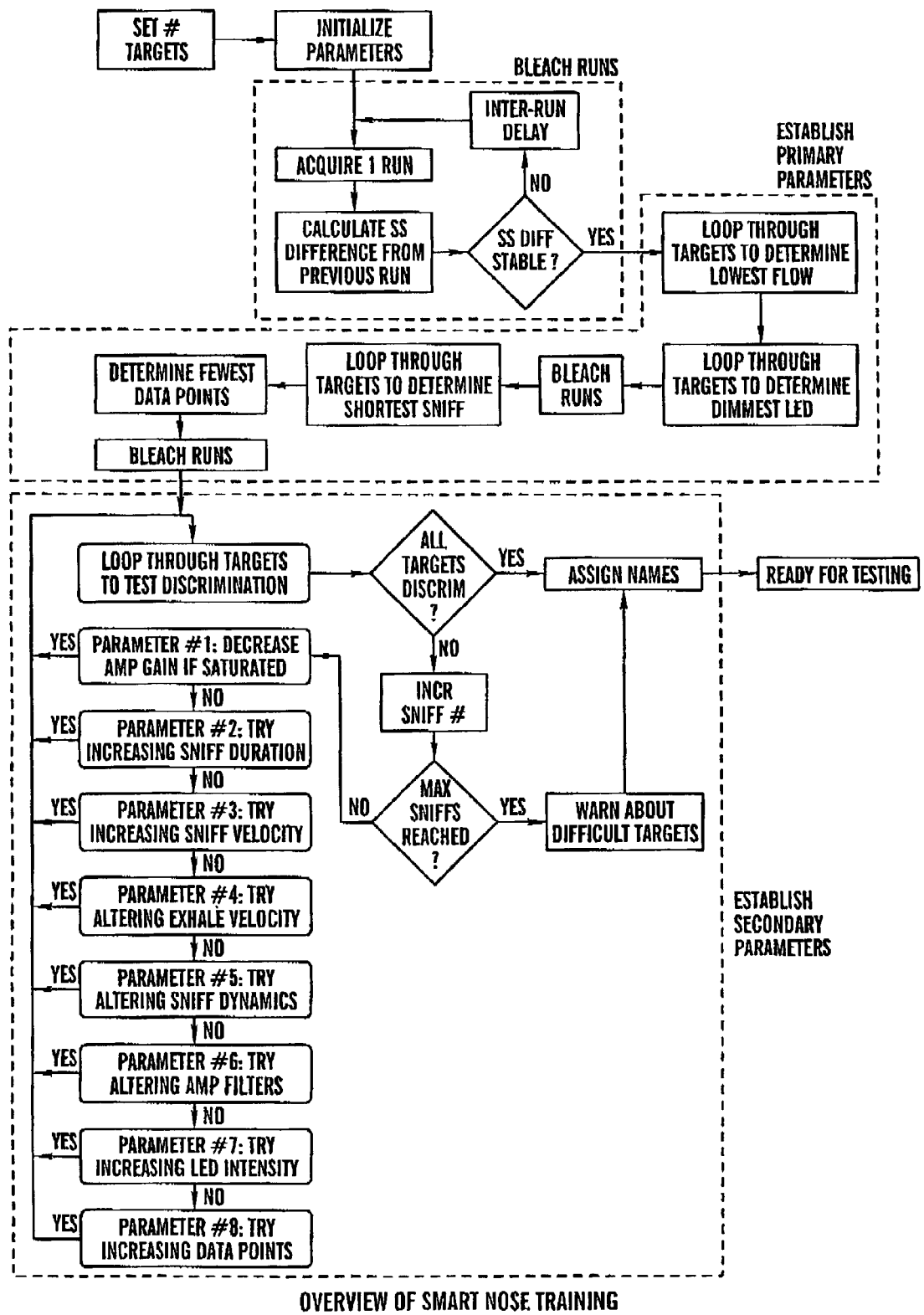
FIG. 6 is a schematic flowchart of a sensor training method employed in the sensing method of the present invention.
Figure 8:
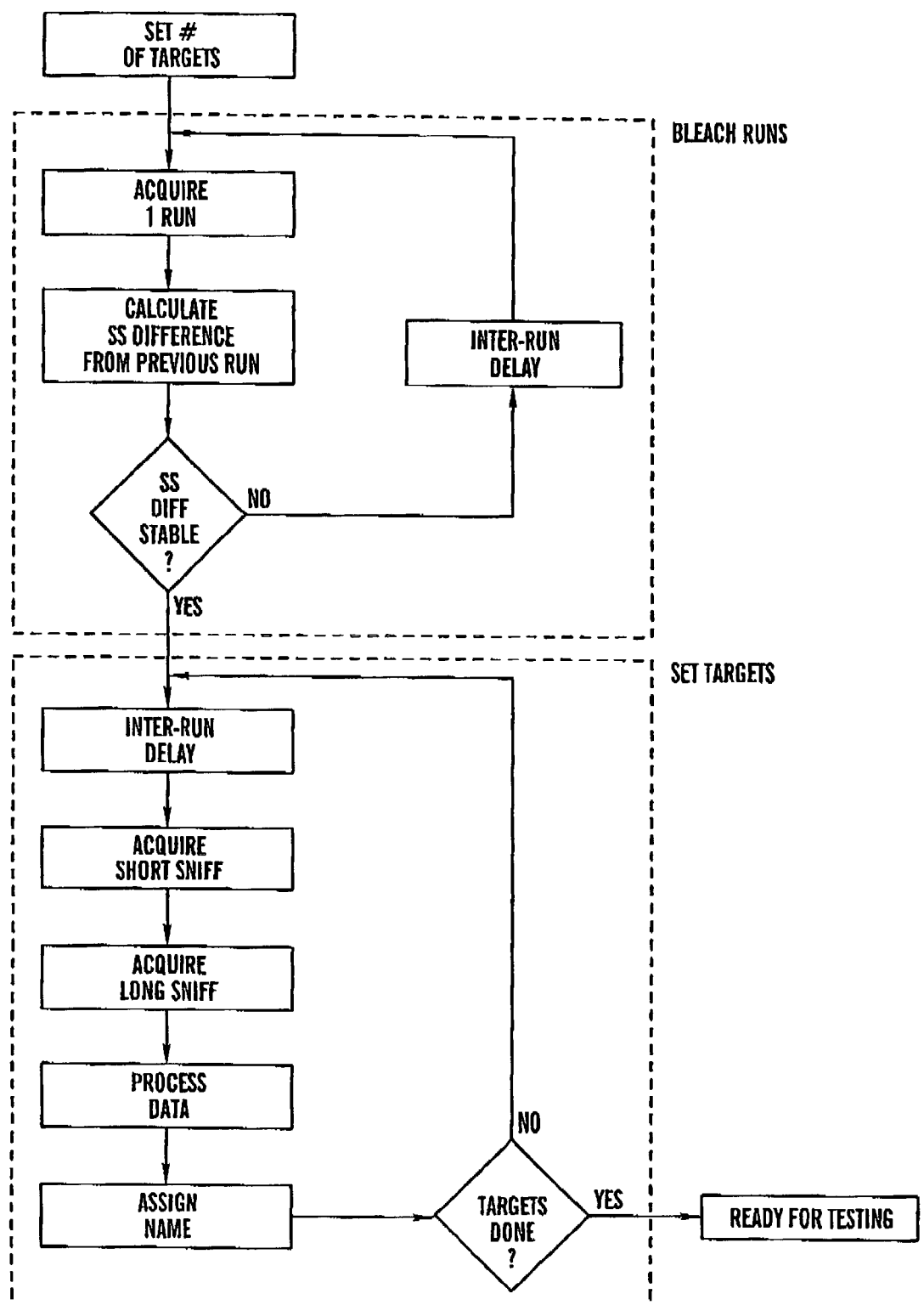
FIG. 8 is a schematic flowchart example of the sensor training method employed in the smart sensing method of Example 3.

FIGS. 6 and 8 provide schematic flowcharts of typical training methods employed with the sensing device of the present invention.

Target samples of known analytes (odors), either pure compounds or complex mixtures, are required for training the sensing device and identifying unknown analytes in sampled fluids. Training samples are typically provided in small, disposable, plastic screw top jars which are vapor tight. A small paper cup insert may be employed with the sample jars as a disposable liner to facilitate cleaning. For typical target training samples, two cotton balls are placed in paper cup that is positioned inside the sample jar and analyte odor-generating material is typically added either as a liquid or solid (e.g. camphor, chocolate, cloves, and orange peels). The cotton provides a high surface area for promoting evaporation and prevents unrestrained liquid samples from spilling.

For all training runs, initially a clean air test sniff is first taken by initiating the automated sampling sequence which provides for turning on the LEDs, taking digitized data from the photodiodes, measuring background fluorescence and storing this in memory, turning on the sniff pump, turning off the pump, terminating data acquisition, and turning off the LEDs. The device is then trained for target analytes by placing the target analyte sample container into position and initiating the automated sampling sequence. The sequence of sampling and data acquisition events for target analytes is the same as for the air baseline sample. This training sequence is repeated for each target analyte of interest and response data are stored in the microcontroller computer RAM memory module.

Figure 7:
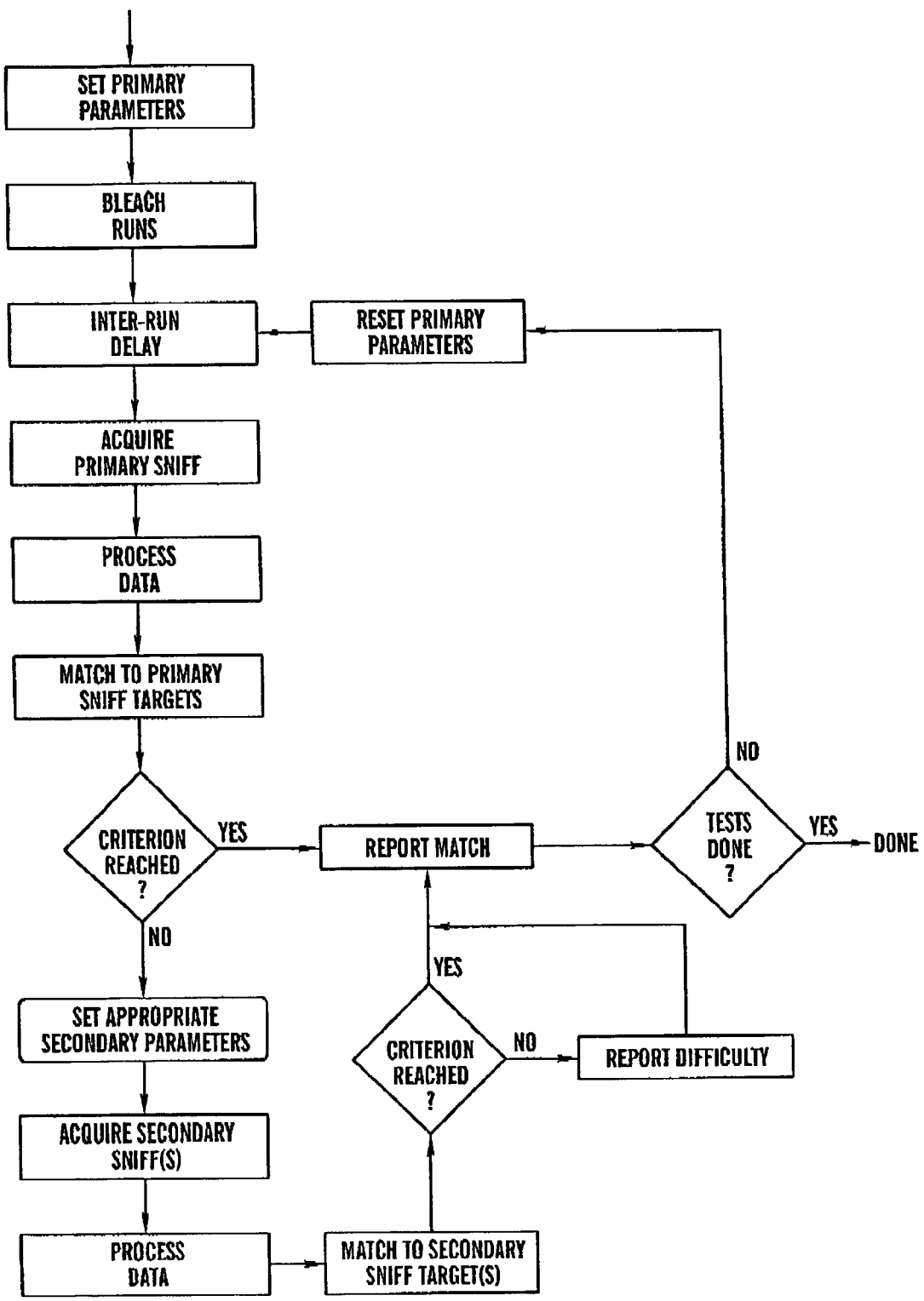
FIG. 7 is a schematic flowchart of an analyte test method employed in the sensing method of the present invention.
Figure 9:
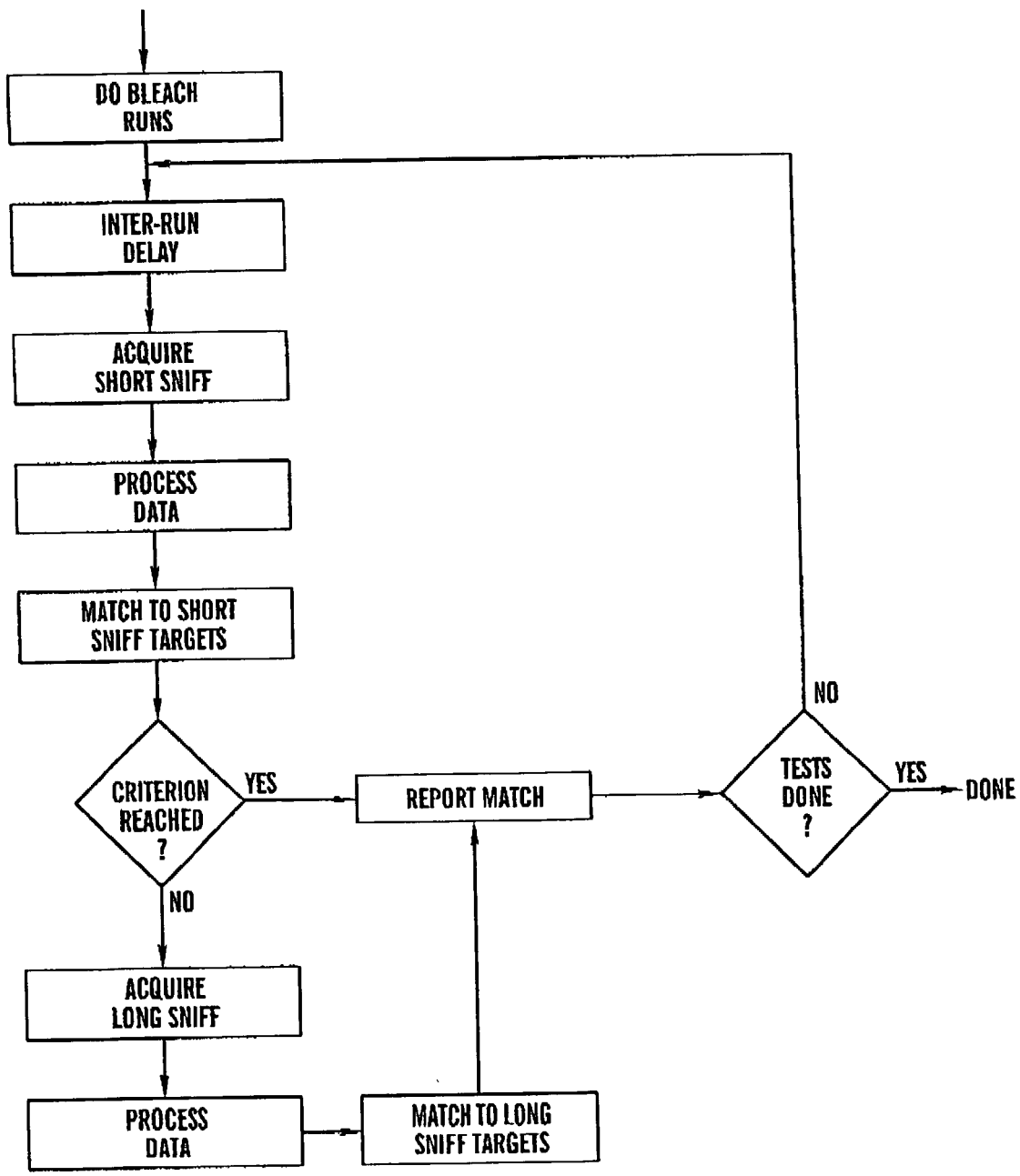
FIG. 9 is a schematic flowchart example of the analyte test method employed in the smart sensing method of Example 3.

FIGS. 7 and 9 provide schematic flowcharts of typical sampling procedures employed with the sensing device of the present invention.

The sequence of steps for sampling unknown analytes are similar to the training runs described above. A typical sampling sequence is shown schematically in FIG. 7. The entire sampling sequence is controlled by a microcontroller computer embedded in the sensing device. An example of a typical sampling run sequence in a device with inhalation and exhalation fans and amplifier electronics from Red Shirt Imaging Inc. (Fairfield, Conn.) is as follows:

1. Set inhalation and exhalation fan valves in partial exhale mode to prevent uncontrolled diffusion of ambient analytes into sample chamber.
2. LED's are turned on for 100 ms.
3. Amplifier baselines are reset while LED's are on (this zeroes out the background fluorescence).
4. LED's turned off
5. Wait 150 ms
6. Steps 1–3 repeated 5 times to insure amplifier reset is stable.
7. Analyte response run begins
8. Turn on LED's for 100 ms
9. Take an analog data point from each sensor, convert to digital value with 12 (0–4095) bit accuracy, place digital value in memory
10. Turn LED's off
11. Wait 150 ms
12. Repeat steps 8–11 one time (this is before analyte presentation)
13. Switch inhalation valve on and exhalation valve off (see FIG. 6A)
14. Repeat steps 8–11 four times (for 1 sec analyte pulse)
15. Switch inhalation valve off and exhalation valve on (see FIG. 6B)
16. Take 4 more data points (repeating steps 8–11)

17. Analyte presentation and data acquisition phases are complete

In a device with a single fan and DDC112-based amplifier electronics, the following sample timing sequence is followed (shown in FIG. 5):
1. Analyte response run begins
2. Take an analog data point from each sensor in sequence, turning on the LED for that sensor only during a 1 msec integration period, convert to digital value with 20 (0–1, 048,575) bit accuracy, place digital values in memory
3. Wait 100 ms
4. Open odor inlet valve, close clean air inlet valve
5. Repeat steps 2–3 nine times (for 1 sec analyte pulse)
6. Close odor inlet valve, open clean air inlet valve
7. Analyte presentation and data acquisition phases are complete After analyte presentation and data acquisition using either device, evaluation circuits and algorithms characterize the spatio-temporal response data of the array either via pattern recognition algorithms, template matching, a neural network, statistical analysis, or other analytical methods for analyte identification. Results may be displayed on screen, spoken by voice synthesis, or plotted as a three-dimensional response surface of fluorescence changes from each sensor at each time point during sampling. If sensing device is on robotic vehicle, results are processed for feedback control and decision is made to stay on course or execute an appropriate maneuver.

Figure 5:
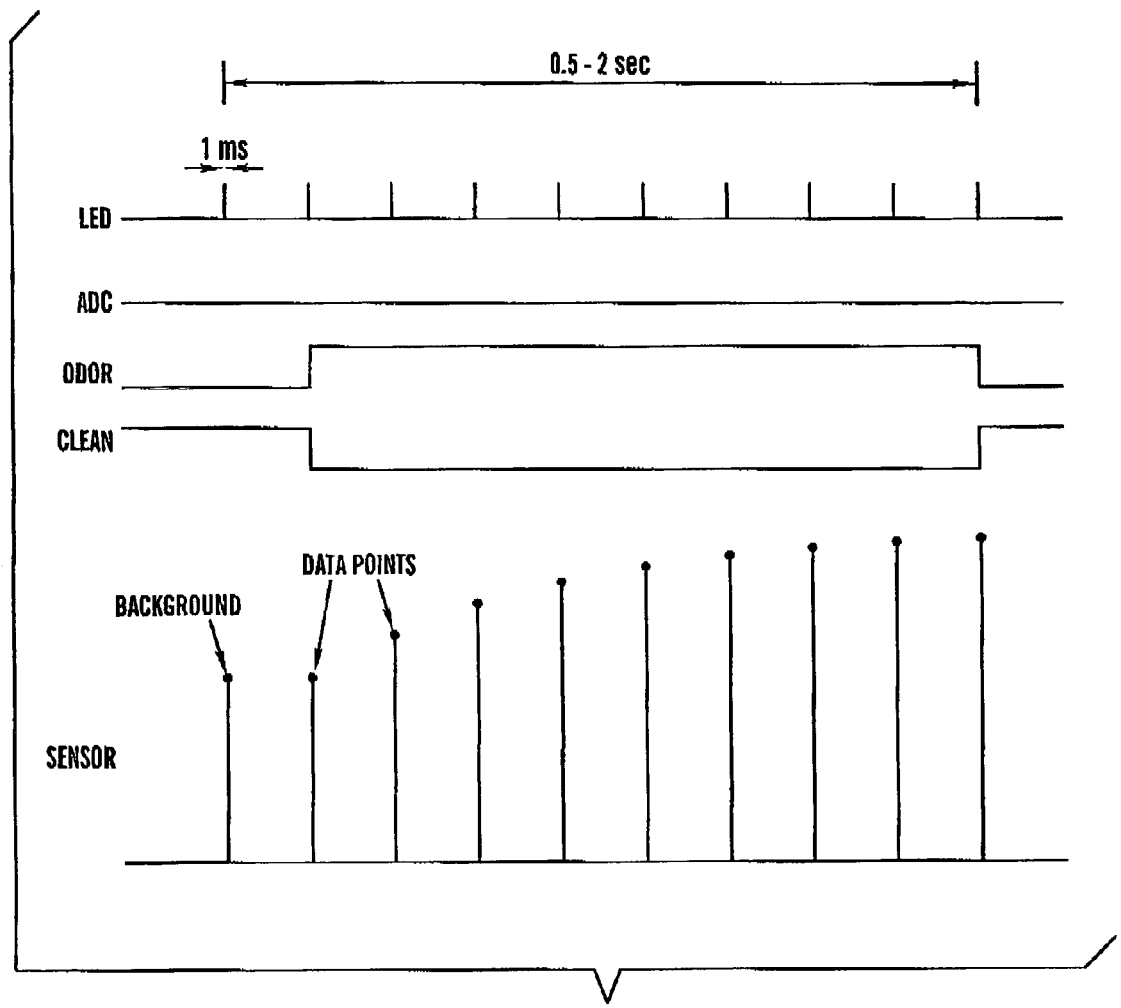
FIG. 5 is a schematic of an example of a data acquisition timing diagram used in the sensing method of the present invention.

FIG. 5 shows an exemplary timing diagram to illustrate this latter sequence of events that occur during sampling of an air sample. Upward deflections in the LED line indicate the time when the LEDs are illuminated. Upward deflections in the ADC line indicate the time when the Analog-to-Digital Conversions occur for all channels. For the "Odor" and "Clean" lines, an upward deflection indicates the time when airflow valve is open so that the air sample comes from the indicated source. Downward deflection indicates the time when the valve is closed. The "Sensors" line indicates a schematized signal generated by a sensor and the small dots indicate the points in the signal when the analog-to-digital conversion occur.

Optionally, where multiple samples or complex mixtures containing multiple analytes are being sampled, the above sampling steps may be repeated with data sampling and acquisition modifications based on intelligent feedback via smart algorithms. Thus, real-time, on-the-fly feedback can dynamically modulate either LED, photodiode, or sniffing hardware settings, or alternatively, analyte sampling parameters such as, sample duration, rise time, relaxation time, delay from previous sniff, amplifier gain and time constants may be modified. These modifications may be imposed on the next data acquisition within the same sampling trial until detection and identification of the analyte occurs.

The steps taken in training the device and testing for analytes, including data analysis and matching, are shown in the flow charts of FIGS. 6 and 7 and the timing diagram of FIG. 5. Both FIGS. 6 and 7 represent the steps taken in software. The "Acquire" steps are the points where the program controls the hardware to take data as shown in the timing diagram of FIG. 5.

The software program explicitly controls the pre-bleaching phase, the duration for which the LED's illuminate the sensors, the onset of data acquisition, the application of the analyte, the duration of analyte presentation, the cessation of analyte application, the duration of the integration time for each data point, the number of time points, and the interval between time points. All of these parameters can be modulated either by direct operator intervention or, alternatively, by programming the microprocessor with smart algorithms that modify the sampling, data acquisition, or analysis steps through real-time feedback control.

The data are filtered, smoothed, statistically evaluated, compared with libraries of stored templates for odor identification, and/or operated on by any of the algorithms discussed below. The data are typically stored in memory as an array of numbers representing the temporal changes in fluorescence in each sensing channel.

1. Detection Methods and Algorithms

A. Evaluation of Synchrony, Response Signals and Noise Characteristics

To improve the detection and discrimination capability of the sensor of the present invention, additional algorithms may be employed to evaluate "synchrony" of response data across different sensor elements to identify small response signals and reject noise. Evaluation of "synchrony" refers to analyzing how signals coming from identical sensors are similar in the context of when they occur during the sniff cycle. The field that encompasses analytical algorithms is very large and many analytical approaches are available. Due to the innovative features of the present invention, such as the use of multiple detector channels with different wavelengths, use of single or multi-pulsed analyte presentation, and the ability to acquire data from sensor elements in parallel rather than serially, the design of the present invention enables consideration of a number of alternative algorithms beyond those that are conventionally used in artificial noses. Additionally, in preferred embodiments algorithms which are based on biological circuits may be employed (see J. White, et al., *Biol. Cybern.* 78:245–251 (1998); J. White, et al., *Anal. Chem.* 68(13):2191–2202 (1996), which publications are incorporated herein by reference in their entirety). The device of the present invention may employ synchronously occurring signals in some embodiments since sensor response data are acquired simultaneously in parallel.

B. Detection Algorithms

The degree to which the response matrix of a test substance corresponds to one of the target analyte library matrices stored during the sensor training phase can be evaluated in a number of ways.

In one preferred embodiment, the rising phase of each sensor signal is fit by an exponential function containing two parameters describing the signal amplitude and rate of change. A matrix of these parameters is then used to represent the sensor array response. Matches are determined from the sum of the squared differences between each parameter in the test matrix and the training matrix. The smallest sum is used to identify the best target analyte match.

In an alternative preferred embodiment, a supervised, for example back propagation, neural network approach may be employed. Examples of these methods are provided in J. White, et al. "Rapid Analyte Recognition In A Device Based On Optical Sensors And The Olfactory System", *Anal. Chem.* 68(13):2191–2202 (1996) and S. R. Johnson, et al., "Identification Of Multiple Analytes Using An Optical Sensor Array And Pattern Recognition Neural Networks", *Anal. Chem.* 69(22):4641–4648(1997).

In another preferred embodiment, analytical circuits based on the olfactory system may be employed as disclosed by J. White, et al., "An Olfactory Neuronal Network For Vapor Recognition In An Artificial Nose", *Biol. Cybern.* 78:245–251(1998).

In another preferred embodiment, unsupervised neural networks may be used. Principle component analysis and multidimensional scaling are, in effect, unsupervised statistical methods for reducing dimensionality. Generally, unsupervised neural networks organize high dimensional input data into lower dimensional representations. For example, assuming one embodiment of the present device with 32 sensors and 20 time points, a total of 640 data points may be collected. In this embodiment, each analyte presentation can thus be thought of as a point in 640-dimension space, which, while difficult to visualize, may be mathematically manipulated. By averaging across sensors and time, the data dimensionality may be reduced, but typically data dimensionality above about four dimensions is rather difficult to visualize.

Self-organizing maps (SOMs) are unsupervised neural networks that reduce data dimensionality. Such SOM methods are attractive for representing artificial olfactory system data because they give a visualization of "odor space". In other words, a map of relationships among various analytes can be produced during training; then during testing, the location of a test analyte on the 'map' indicates the relationship of the analyte with respect to this 'space'. Thus, SOMs may help to visualize relationships among analytes, rather than simply indicating the similarity of an unknown analyte to a target. Examples of SOM approaches which may be particularly useful for analyte detection, discrimination and identification are disclosed by T. Kohonen. et al., "SOM-PAK: The Self-Organizing Map Program Package", Report A31, Helsinki University of Technology, Laboratory of Computer and Information Science, Espoo, Finland (1996) and T. Kohonen, *Self-Organizing Maps*, Series in Information Sciences, Vol. 30, $2^{nd}$ ed., Springer-Verlag, Heidelberg (1997), which publications are incorporated herein by this reference.

C. Sampling and Detection Parameter Modulation

Upon evaluation of the response matrices generated by the standards used for training, modifications in sniffing parameters, gain settings, and/or filter settings may be made for actual sampling of ambient fluids. In a standard operating mode, these modifications may be made through interventions of an operator who manually changes sampling and data acquisition parameters through the programmable microcontroller or by keyboard entry. In alternative smart operating modes described in subsequent sections, these modifications may be made automatically, on-the-fly by smart sampling and detection algorithms that direct microcontroller operations.

Whether and how much such modification improve sensing performance may be evaluated by examining sensor responses after feedback and determining, by some predetermined or analytically-derived criterion, whether current sample data are better or worse than data obtained on a previous run. Modifications may also consist of differentially weighting the influence of sensors, so that those sensors that give the best signals have a greater impact in the recognition algorithms. This can be done in a number of ways, such as eliminating sensors that give little or no signal so as to reduce noise, normalizing the remaining signals to some standard value in order to use the maximum range available, or changing the analyte sampling and stimulus acquisition paradigm to optimize sniff sampling parameters.

D. Smart Mode Operation

One example of an embodiment of the smart mode sampling capability of the present invention is where the number and duration of analyte samples taken during a sample session are controlled by way of real-time feedback and control loops for improving detection, discrimination and identification of analytes. In other embodiments, alternative smart mode parameters and device sampling configurations may be manually or automatically selected during training and sampling via device menu options. Smart mode sampling configurations may be used alone or in a variety of combinations and permutations. In one anticipated embodiment, an automated training algorithm may be employed to optimize parameter selection and sampling configuration in order to provide the best detection and discrimination capability for specific analytes of interest. Specific examples of alternative smart mode sampling options and parameter configurations are described below.

1. Sampling Parameters

A. Sniff Parameters.

i) Sniff Duration.

For sensors that respond slowly to a particular analyte, increasing the sniff duration leads to increased signal amplitude and hence improved detection accuracy.

ii) Number of Sniffs.

In the simplest implementation, signals across multiple sniffs may be averaged to improve signal-to-noise. However, different sensors exhibit different long-term responses to multiple sniffs (providing either increasing signal, decreasing signal, or constant signal over a series of sniffs). Monitoring these changes over sniffs (rather than simply averaging the signals) could provide additional information for analyte discrimination.

iii) Sniff Dynamics (Rise Time, Fall Time).

The rate and extent of sample chamber valves opening and closing may be controlled to modify sampling (sniff) dynamics.

Changing the sniff dynamics may enhance differences in the rising and falling phases of the sensor response.

iv) Sniff Velocity.

In one anticipated embodiment, a digital-to-analog line may be used to control a transistor that changes the voltage supplied to the sniff fan and thereby alter fan velocity. Changing sniff velocity, in conjunction with changes in sniff duration, can provide optimized exposure of the sensors to particular analytes.

v) Exhalation Velocity.

As with changing sniff velocity, a change in exhalation velocity in an embodiment with two fans would alter the rate at which analyte is purged from the sensors. In a system with a single fan, the velocity of that fan between sniffs can be similarly altered. The dynamic sensor response may then be monitored in subsequent sniffs for improved analyte discrimination.

B. LED Intensity.

While higher LED intensity leads to more rapid photobleaching and sensor degradation, it also tends to yield larger sensor response signals during analyte exposure. In one smart mode embodiment, normal sampling would be made at lower LED intensity and, where small response signals are present, LED intensity may be increased incrementally until reliable response signals are produced for analyte detection. This smart mode would tend to extend sensor lifetime by operating at minimum LED intensity to reduce photobleaching.

C. LED Wavelength.

The excitation wavelength of the LED may be modulated. LEDs are commercially available that produce three separate wavelengths. The wavelength of conventional LEDs may be modulated by changing applied voltage and flicker frequency. The capability for changing LED wavelength may permit the device to optimally excite the sensors and to change that excitation over sniffs to improve discrimination.

D. Amplifier Gain Settings.

Under typical sampling conditions, the highest gain settings are employed. Under such a condition, some analytes produce sensor signals that saturate the amplifier. By providing for adjustment of gain settings during smart mode sampling, if an amplifier channel saturates, an additional sniff at a lower gain setting would provide more accurate time course and amplitude information.

E. Amplifier Temporal Filter Settings.

In embodiments incorporating amplifiers containing integral temporal filters, changing the filter settings may be used to improve the signal-to-noise characteristics of the individual sensor channels. As shown in FIG. 5, data acquisition and A/D conversion are closely correlated with LED pulse timing. However, some detection enhancement may be achieved by modifying the timing of data acquisition during an LED pulse for improved signal discrimination for specific analytes; modulation of this parameter may therefore improve detection and identification of certain analytes.

F. Gain and Temporal Filter Settings for Individual Channels.

While one current embodiment of the amplifier electronics allow manipulation of gain and filter settings globally (i.e. gain and filter changes apply to all channels simultaneously), in alternative sensor embodiments, individual sensor channels may also be manipulated for smart mode sampling and detection.

Smart mode training and sampling procedures using these and other parameter variations are discussed in greater detail below.

2. Smart Mode Training

FIG. 6 provides a schematic flowchart for smart mode training procedures. Smart mode training is divided into two main sections: first, the parameters defining the "primary" sniff are determined, followed by a determination of parameters for any "secondary" sniff(s) that may be necessary. The constraints for the two sets of parameters are different: The primary sniffs are applied at regular intervals over long periods of time and should have minimum impact on sensor lifetime since they expose the sensors to as little light as possible to reduce photobleaching and to as little analyte as possible to prolong sensor lifetime and shorten recovery time. Secondary sniffs are intended to generate signals that produce better discrimination.

A. Photobleaching and Bleach Runs

Exposing a fluorescent sensor to prolonged excitation light produces photobleaching, decreasing the fluorescent output of the sensor. This fluorescence recovers over time after the excitation light is turned off. In embodiments where sensors are exposed to prolonged excitation light during acquisition of response data at variable intervals, there appears to be more variability in sensor response. Preferably, response data are acquired at regular 15 second intervals. Sensor bleach runs establish this regular interval before data are actually acquired. The bleach runs are repeated until the signals from the sensors stabilize. In preferred embodiments using short excitation light exposures (1–5 ms), variability across sniffs due to photobleaching is greatly reduced.

In embodiments using longer excitation light exposure, bleach runs are acquired either with or without sniffing a blank air sample. The response matrices from these runs are compared to the previous run by calculating the sum of squares (SS) difference for all data points. For the first run, the comparison is to a matrix of zeroes. If the SS difference is stable, where successive SS differences change little, training target sampling is initiated. If the SS difference is unstable, an 15 second inter-run delay time is used and then the bleach run is repeated. While the operator may evaluate the SS difference stability visually, this process may be automated by setting a criterion which provides for minimum changes in successive SS differences; when that criterion is reached, the program continues and training target sampling is initiated.

B. Establishment of Primary Parameters

Device parameters are initialized to settings that should give discriminating signals upon analyte exposure. For example, the LEDs are turned up to the highest intensity by sending the highest voltage possible out the D/A line to the LED controller and a long sniff at high flow is acquired by sending a voltage signal through the D/A control line to control the inhale fan. This section of the program finds the minimum values for these parameters that lead to discrimination of analyte signals from air. In the flow chart shown in FIG. 6, the rectangles with rounded corners represent subroutines of several steps that are described below. The "criterion" referred to here is initially determined through experimentation with a particular set of sensors and can be subsequently incorporated into the programmable microcomputer for automatic control. In the descriptions below, "SS difference" refers to sum-of-square difference between individual data points in the response matrix, or between parameters of the exponential fit described above.

1. First, sensors that do not respond to any of the analytes are found. Data from all analytes and air are acquired.

For each sensor, the SS difference between air and each analyte is calculated. If a sensor does not produce a SS difference value above criterion for any of the analytes in the training set, that sensor is removed from consideration for subsequent training and testing.

2. Second, the lowest permissible sniff flow is determined:
  a) Take single sniffs of all analytes and air.
  b) Calculate SS differences between response matrices of each analyte and air
  c) If SS difference values are all above a criterion, reduce sniff flow velocity by 10% (i.e., reduce voltage of D/A by 10%) and repeat from step 1, otherwise increase flow velocity by 10% (unless flow is already maximal) and stop.
  d) All data are saved to flash (non-volatile) memory for possible later use.

3. Third, a similar procedure is used to determine the dimmest LED setting:
  a) Take single sniffs of all analytes and air.
  b) Calculate SS differences between response matrices of each analyte and air
  c) If SS difference values are all above a criterion, reduce LED intensity by 10% (i.e., reduce voltage of D/A by 10%) and repeat from step 1, otherwise, increase LED intensity by 10% (unless LED intensity is already maximal) and stop.
  d) All data are saved to Flash Memory for potential use later.

e) Because the level of excitation light is likely reduced by the preceding steps, another set of bleach runs is then taken.

4. Fourth, the shortest sniff is determined:
   a) Take single sniffs of all analytes and air.
   b) Calculate SS differences between response matrices of each analyte and air
   c) If SS difference values are all above a criterion, reduce sniff duration by half (i.e., open sniff valve for half the time) and repeat from step 1, else double the sniff duration (unless sniff duration is already maximal) and stop.
   d) All data are saved to Flash Memory for possible later use.

5. Fifth, the fewest time points to collect is determined. Start with the short sniff data stored in the previous step (it is not necessary to collect new data here):
   a) Start by considering data up to the time point just after the sniff begins.
   b) Calculate SS differences between response matrices of each analyte and air
   c) If SS difference values are all above a criterion, stop. Else consider 1 additional time point (unless the number of time points is already maximal) and repeat from step b.
   d) Because the number of time points to collect is likely reduced by the preceding steps, another set of bleach runs is taken.

The result of the "Establish Primary Parameters" section is now the lowest flow, dimmest LEDs, shortest sniff, and fewest time points necessary to discriminate analyte signals from air.

C. Establishment of Secondary Parameters

The goal of this section is to determine the parameters of one or more subsequent sniffs, if necessary, that will improve discrimination of analytes that are not discriminating based on the primary sniff alone. The parameter adjustments occur only for the analytes that are difficult to discriminate. The "criterion" referred to here is determined through experimentation with the particular set of sensors used. It may be different from the criterion used in the primary parameters section above.

Step 1. Data from all analytes and air are acquired. If this is the first time through this step, only primary sniffs are defined and acquired. These data are saved as the primary sniff targets. The SS differences between each pair of response matrices is calculated. This includes responses to secondary sniffs, if defined. If all SS difference values are above a criterion, all targets are deemed to be capable of discrimination. Names are assigned to the targets and the system is ready for testing. Otherwise, go to step 2.

All of the following steps are applied only to those analytes that fail to meet the criterion of step 1.

Step 2. If the number of sniffs for the "difficult" target analytes has reached a user-determined maximum, this value will probably be on the order of 3 or so sniffs, warn the user about the difficult targets. Assign names to the targets and go to testing.

Step 3. Increment the sniff number by 1 Each parameter block attempts to optimize the stated parameter for each of "difficult" targets. The parameter blocks may be ordered as shown so that the first five parameter modulations do not increase the amount of excitation light exposure.

1. Parameter #1

Difficulty in discrimination may be due to saturation of the amplifier channel. This is apparent if the signal from any amplifier channel reaches a value of approx. 2000 or −2000 and stays at that level for 2 or more time points. The Red Shirt Imaging, Inc. amplifier has gains of 1000×, 200×, 50×, and 1×. If saturation occurs, follow the following steps:
   a) Decrease the amplifier gain one step and acquire data from the difficult targets.
   b) If the SS difference between the difficult targets is now above criterion, retain this gain setting for these difficult targets and go to step 1. If the amp gain is at minimum (i.e., none of the lower amp gains improved discrimination), go to step c. Otherwise, repeat from step a.
   c) If any of the gain settings produced some improvement, retain this setting. Otherwise, reset parameter to original value and go to next parameter block.

2. Parameter #2

Since data from longer sniffs may have been acquired in the "Establish Primary Parameters" section, investigate those stored data for improved discrimination. If the SS difference between the difficult targets for any of the longer sniffs is above criterion, retain the best setting and go to step 1. Else, go to the next parameter block. If some improvement was made (but still below criterion), retain the best setting. Otherwise, reset parameter to original value.

3. Parameter #3

Since data from higher sniff velocities may have been acquired in the "Establish Primary Parameters" section, investigate those stored data for improved discrimination. If the SS difference between the difficult targets for any of the higher sniff velocities is above criterion, retain the best setting and go to step 1. Else, go to the next parameter block. If some improvement was made (but still below criterion), retain the best setting. Otherwise, reset parameter to original value.

4. Parameter #4

For a sniff, the valves are normally opened and closed abruptly (i.e., the PWM signal to the servo changes from one position to the other instantly). For some analytes and some sensors, opening and/or closing the valves more slowly may help produce discriminating signals. To open/close the valves slowly, the PWM signal to the servos will be changed in smaller steps over time. In other words, instead of opening the valve fully at a particular time point, open the valve in two steps over two time points by opening the valve half way for the first time point, then fully the next. For an even slower opening, use three steps: open $\frac{1}{3}$ at one time point, $\frac{2}{3}$ the next, and fully the next. A maximum of 5 steps will likely be sufficient.
   a) Slow sniff on rate by increasing the number of opening steps by 1; acquire data from the difficult targets.
   b) If the SS difference between the difficult targets is now above criterion, retain this sniff setting for these difficult targets and go to step 1. If the number of sniff steps is at maximum (i.e., none of the fewer steps improved discrimination), go to step c. Otherwise, repeat from step a.
   c) Reset number of steps to original value.
   d) Slow sniff off rate by increasing the number of closing steps by 1; acquire data from the difficult targets.
   e) If the SS difference between the difficult targets is now above criterion, retain this sniff setting for these difficult targets and go to step 1. If the number of sniff steps is at maximum (i.e., none of the fewer steps improved discrimination), go to step f. Otherwise, repeat from step d.

f) If any of the sniff on or off settings produced some improvement, retain the best setting. Otherwise, reset parameters to original values and go to next parameter block.

5. Parameter #5

Filters in the Red Shirt Imaging amplifiers are normally set at DC—no high-pass filtering at all. Adding high-pass filtering may help to accentuate the rising or falling phases of the sensor signal, leading to improved discrimination. The filter settings available on the Red Shirt Imaging amplifier have time constants of 500 ms, 100 ms, and 30 ms (increasing the high-pass cut-off frequency).

a) Increase the amplifier high-pass cut-off one step and acquire data from the difficult targets.
 b) If the SS difference between the difficult targets is now above criterion, retain this filter setting for these difficult targets and go to step 1. If the filter cut-off is at maximum (i.e., none of the lower filter settings improved discrimination), go to step c. Otherwise, repeat from step a.
 c) If any of the filter settings produced some improvement, retain the best setting. Otherwise, reset parameter to original value and go to next parameter block.

6. Parameter #6

Since data from brighter LEDs may have been acquired in the "Establish Primary Parameters" section, investigate those stored data for improved discrimination. If the SS difference between the difficult targets for any of the brighter LED settings is above criterion, go to step 1. Otherwise, go to the next parameter block. If some improvement was made, but it is below the criterion, retain the best setting. Otherwise, reset parameter to original value.

7. Parameter #7

Since data from more data points may have been acquired in the "Establish Primary Parameters" section, investigate those stored data for improved discrimination. If the SS difference between the difficult targets for any of the increased data points is above criterion, go to step 1. Otherwise, go to the next parameter block. If some improvement was made, but it is below the criterion, retain the best setting. Otherwise, reset parameter to original value.

8. Parameter #8

It is possible that changing fan velocity (exhale fan velocity in two fan systems) between sniffs may improve signals for the second sniff. This parameter block is placed last in order to attempt to add to improvements produced by previous parameter blocks that are still below criterion.

a) Decrease exhale velocity by 10% (i.e., decrease voltage to exhale fan via D/A lines and LM317 voltage controller) and acquire data from the difficult targets.
 b) If the SS difference between the difficult targets is now above criterion, retain this velocity setting for these difficult targets and go to step 1. If the velocity is at minimum (i.e., none of the lower velocities improved discrimination), go to step c. Otherwise, repeat from step a.
 c) Reset velocity to original value.
 d) Increase exhale velocity by 10% and acquire data from the difficult targets.
 e) If the SS difference between the difficult targets is now above criterion, retain this velocity setting for these difficult targets and go to step 1. If the velocity is at maximum (i.e., none of the higher velocities improved discrimination), go to step f. Otherwise, repeat from step d.
 f) If any of the velocity settings produced some improvement, retain the best setting. Otherwise, reset parameter to original value. If the program reaches this point without reaching criterion, then none of the parameter changes improved discrimination. Warn the user about the difficult targets, assign names to the targets, then go to testing.

D. Smart Nose Testing

FIG. 7 provides a schematic flowchart for smart mode testing procedures. Smart Nose testing a single analyte can occur in two stages. First, a primary sniff is taken and, if the primary sniff produces a good match to a target, that match is reported. Secondly, if the primary sniff does not produce a good match, one or more secondary sniff(s), if defined by training, are taken. If a match criterion is not reached, the matching difficulty is noted and the closest match reported. If the goodness criterion is reached, the match is reported.

1) Testing begins with parameters determined by "Establish Primary Parameters" Section of Training.
 2) Take bleach runs, if necessary, as described under Training.
 3) After an inter-run delay, acquire a primary sniff and process the data.
 4) The primary sniff data are matched to the primary sniff targets by calculating the SS difference to each target (as described above).
 5) If "goodness" criterion is reached, report the match. Continue testing.
 6) Otherwise, does target with lowest SS difference have secondary sniff(s) defined? If not, note difficulty, report this target and continue testing.
 7) Otherwise, set the appropriate secondary parameters.
 8) Acquire the secondary sniff(s) and process the data.
 9) The secondary sniff data matrix (or matrices, if more than one sniff) is/are matched to the secondary sniff targets by calculating the SS difference to each target.
 10) If the "goodness" criterion is reached, report the match. Otherwise, note difficulty, report closest target, and continue testing.

The photodiodes employed in the present invention are intrinsically more sensitive than and have larger dynamic range than individual pixels of conventional CCD camera detectors. The detection surface area of individual sensor photodiodes in the present device is larger than individual pixel areas of conventional CCD camera detectors. Additionally, due to the surface area of the LEDs and photodiodes employed in the present invention, larger sensor element areas may be employed and sampling is conducted over a larger geometric surface area of individual the sensor elements. Furthermore, the innovative fluid permeable, high porosity high surface area sensor substrates of the present invention, further enhance sensor response signals due to a substantial increase in sensor surface area to volume ratios and the volumetric sampling of sensor response signals generated within a three-dimensional substrate-sensor volume.

Another source of increased sensitivity in embodiments using the Red Shirt Imaging amplifier is the capability to reset the baseline of the amplifier after turning on the excitation light in order to look only at fluorescence differences above background, rather than the background illumination itself. Thus we are not limited by having to reduce gain or light intensity to prevent detector saturation as observed with conventional CCD camera detectors. These amplifiers are specifically designed for resetting signal baseline in order to look at small fluorescence changes on a large background. In embodiments using DDC112-based amplifier electronics, the large dynamic range of the AD circuit (20 bits) also enables monitoring of small changes in fluorescence on large fluorescent backgrounds. In addition, readout from the photodiodes employed in the present invention is intrinsically less noisy than readout from pixels from CCD camera detectors employed in other devices because the readout speed per channel with the present invention is lower than that of CCD camera detectors and higher signal-to-noise ratios are achieved.

The enhanced sensitivity of the present sensors may be further augmented by utilizing multiple layers of sensing material 'suspended' in the air stream, employing larger surface area sensor elements and larger surface area photodiodes, and/or using replicates of multiple identical detectors in the sensor array from which signals are combined electronically. Replicates of different sensing materials may be incorporated into different sensor channels. Using replicates provides advantages not only with respect to the duplication of data to verify measurement reproducibility, but also with regard to reducing non-correlated noise from electronic components such as amplifiers.

EXAMPLES

Example 1

TABLE 2

A Summary of DNA Used

| DNA | Length (b or bp) | Structure | Melting temp (° C.) | Source |
|---|---|---|---|---|
| PblueScriptSK | 29000 | Supercoiled | | Stratagene |
| DS001 | 33 | AT hairpin, 14 bp ds | 51.3 | synthesized |
| DS002 | 33 | GC hairpin, 15 bp ds | 95.0 | synthesized |
| DS003 | 33 | 2 ss loops w/3 bp ds | 45.4–46.8 | synthesized |
| AJ001 | 22 | 4 ss loops w/2–3 bp ds | 26.6–35.6 | synthesized |
| Oligo dT | 15 | Linear | | Perkin Elmer |

Table 2 is a summary of DNA used in the preliminary studies. DS001 indicates the nucleic acid with a sequence TTAATATAAATTTTTCCCAAAAATTTATATTAA (SEQ ID NO: 6); DS002 indicates the nucleic acid with a sequence GGCCGCGCCCGGGGGTTTCCCCCGGGCGCGGCC (SEQ ID NO: 7); DS003 indicates the nucleic acid with a sequence GATCCTTGCTACCCTCTCCTAGGAACGATGGGA (SEQ ID NO: 8); pBluescriptSK was grown in DH5a and purified by ion exchange (Qiagen, Valencia, Calif.; or Promega, Madison, Wis.). To avoid concatamer formation, oligonucleotides DS001–3 were heated to 99° C. for five minutes at a concentration of 10 mM, and allowed to self-anneal slowly before sensor construction. AJ001 is a PCR primer, ACCAGGACCTGACTAAGCAGAT (SEQ ID NO: 5). Predicted structures and melting temperatures were determined using the mfold program (http://bioinfo.math.rpi.edu/~mfold/dna/form1.cgi). Abbreviations: b, base; bp, base pair; ds, double stranded; ss, single stranded.

As an initial test of whether sensors made from DNA and a fluorescent dye respond to odorants, sensors were constructed from a standard 2.9 kb pBlueScriptSK plasmid mixed with YO-PRO dye (Molecular Probes, Inc.).

Figure 10A:
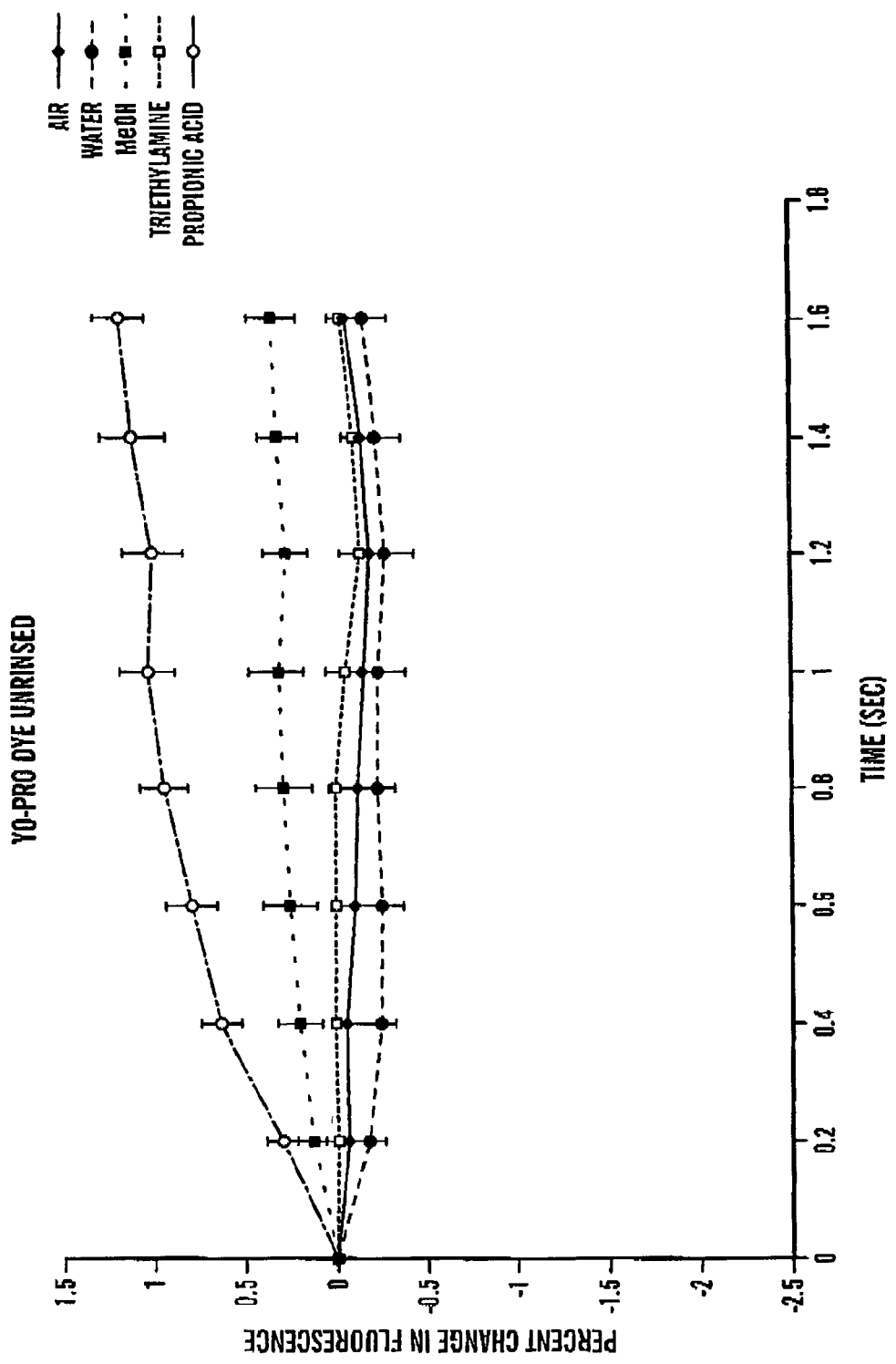
FIGS. 10A–10C show the response profiles of a sensor made from YO-PRO and pBluescript DNA.
Figure 10B:
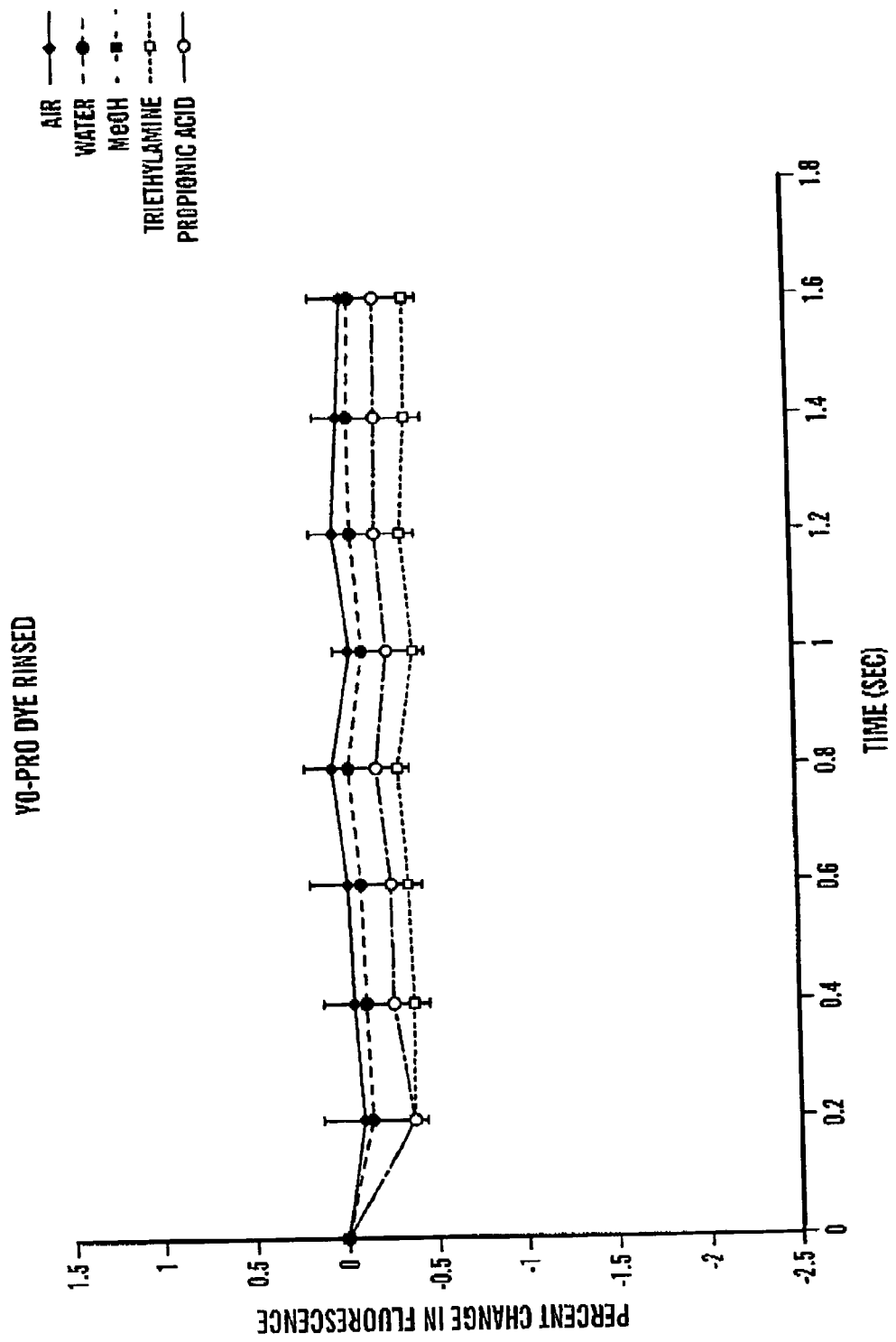

As a control, sensors made from YO-PRO alone, but not rinsed, showed a slight increase in fluorescence upon exposure to propionic acid and a smaller increase with triethylamine (FIG. 10A). In a second control sensor, a five minute rinse with 70% ethanol eliminated these signals (FIG. 10B).

Figure 10C:
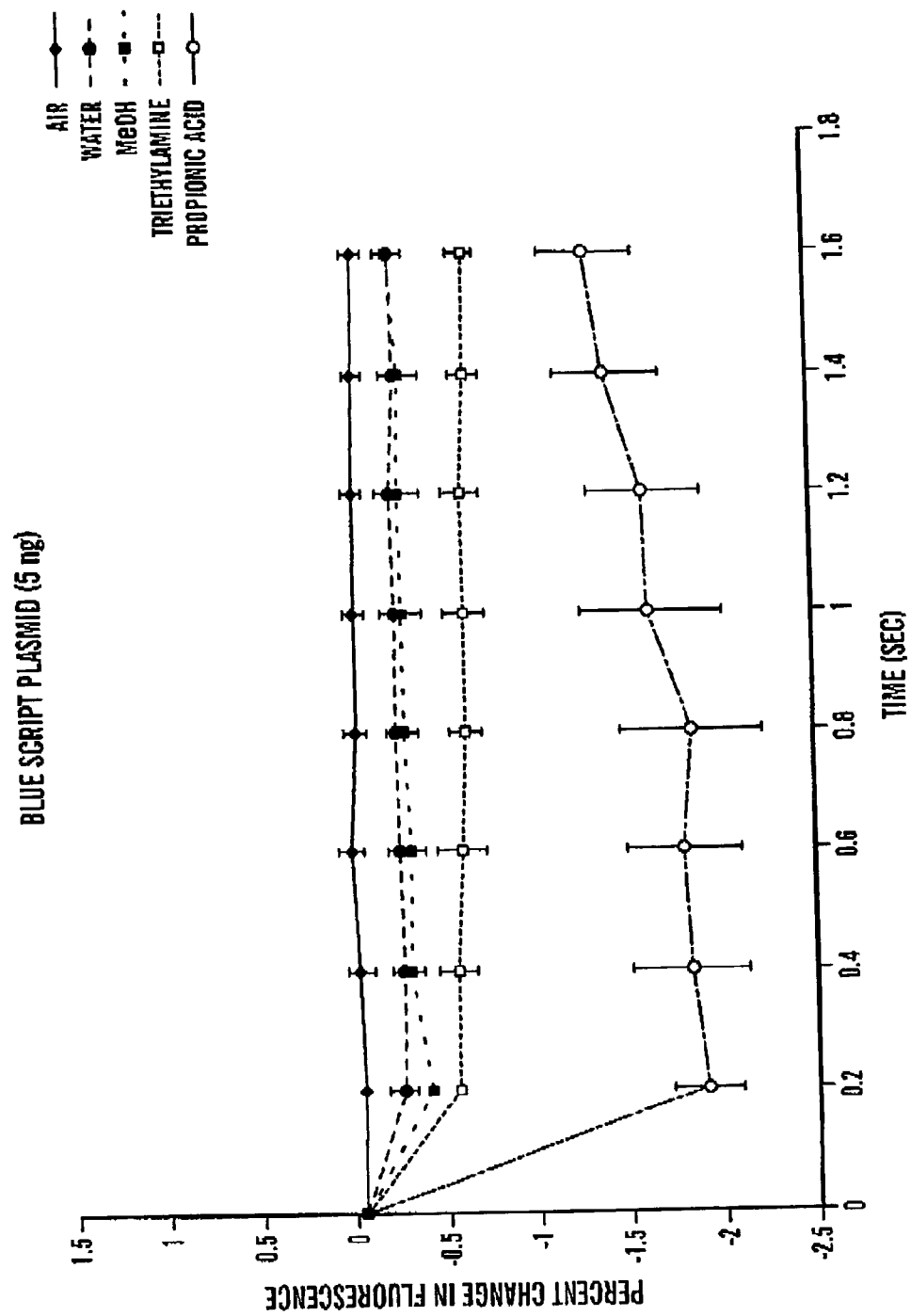

A sensor made by mixing a small quantity of plasmid (5 ng total pBlueScriptSK) with the YO-PRO produced a large and rapid decrease in fluorescence upon exposure to propionic acid, and smaller changes to water, methanol, and triethylamine (FIG. 10C). The DNA effect on YO-PRO does not appear to be a simple enhancement of the YO-PRO signals shown in either FIG. 10. The DNA appears to qualitatively change the odorant response properties of the YO-PRO dye. Odorant dilutions as fractions of saturated vapor were: Water, 1:10; methanol (MeOH), 1:10; triethylamine, 1:100; and propionic acid, 1:10. Each trace represents the mean of 10 replicates; error bars indicate +/−1 S.D. For preliminary experiments with DNA-based odorant sensors, similar methods were used for each type of sensor. Briefly, DNA (Table 2) in solution was diluted to the desired concentration (0.2–40 ng/μl) in TE (10 mM Tris, 0.5 mM EDTA). 20 μl of dilute DNA was mixed with 1 μl concentrated dye stock and incubated at room temperature for 5 minutes. Dye-only controls were made of 1 μl dye stock in 20 μl TE. Sensors were made on a substrate of acid-washed 16xx silkscreen (10 mm×12 mm). DNA/dye mixtures were pipetted onto the substrate and allowed to dry for 25 minutes. Each sensor was rinsed in 70% ethanol for 5 minutes, allowed to dry, then attached to supports on glass coverslips for testing in the present invention.

The DNA effect depended on the quantity of DNA mixed with YO-PRO to produce the sensor (FIG. 11). With DNA quantities up to 80 ng/sensor, increasing the amount of DNA had relatively little effect on the sensor signals, except for a slight increase in the triethylamine signal at 80 ng/sensor. At 800 ng/sensor, the signal amplitude for propionic acid was dramatically reduced, but there was less effect on the triethylamine signal compared to 5 and 10 ng sensors. These data suggest a nonlinear and differential effect of DNA quantity on the sensor response profile. In other words, changing sensor construction parameters such as DNA quantity, while the nucleotide sequence and structure remain the same, can have a significant effect on sensor response profile.

Short sequences of double-stranded DNA. A number of possible mechanisms could lead to the observations from the pBluescriptSK sensors. The plasmid is supercoiled DNA, with complex tertiary structure, which could influence the odorant response properties of the YO-PRO dye. Another possibility is that the YO-PRO odorant response is affected by the DNA sequence surrounding the site of dye intercalation, and the signals shown in FIG. 10 are the statistical average of YO-PRO responses in a large number of possible DNA sequence backgrounds. To begin to test whether changing double stranded DNA sequence per se can produce sensors of different response profiles, two oligonucleotides were synthesized that were composed of solely GC or AT and were designed to form hairpin structures (DS001 and DS002 in Table 2). Although differing significantly in primary sequence, the two sensors made from these hairpins had similar odorant response profiles (FIG. 12). The hairpin sensor responses were also qualitatively similar to the sensors containing small amounts of pBluescriptSK DNA (i.e., 5 ng/sensor in FIG. 10, although the propionic acid signals in the hairpin sensors were about 50% larger.

The hairpin sequences used in these sensors were relatively short, both have 14–15 bp double stranded regions, Table 2, and are not likely to have significant tertiary structure. The observation that sensors made from the GC and AT hairpins showed similar odorant responses suggests that when using YO-PRO dye as a reporter, double stranded sequence alone may not determine the odorant response profile. It is possible that the non-specific nature of the response is in part a result of the YO-PRO dye properties. According to the manufacturer (Molecular Probes, Inc.) YO-PRO is an intercalating dye that shows no sequence specificity. Other dyes, with different staining properties, may yield sensors with different odorant response profiles.

Short sequences of single-stranded DNA. As an initial test of whether simple differences in DNA structure could produce sensors with different response profiles, sequences containing primarily single-stranded DNA were synthesized (DS003, AJ001, and Oligo dT in Table 2) and made into sensors. For example, AJ001 sequence (SEQ ID NO: 4) was synthesized at the Tufts DNA synthesis core facility. The oligomer was diluted to the desired concentration (10 pM/µl, or approx. 30 ng/µl) in TE (10 mM Tris, 0.5 mM EDTA) and 20 µl of dilute AJ001 was mixed with 1 µl concentrated OLIGREEN dye stock solution (dye stock as delivered by Molecular Probes, Inc.; actual concentration unknown) and incubated at room temperature for 5 minutes. Dye-only controls were made of 1 µl dye stock solution diluted in 20 µl TE. A sensor made from the OliGreen dye alone showed a decrease in fluorescence upon exposure to propionic acid, but little change with other odorants (FIG. 13). This response was not eliminated with longer rinse times of 10 and 15 min. Sensors made from Oligo dT (FIGS. 13A and 13B) and DS003 (FIG. 13C) showed enhanced signals to propionic acid and the other odorants tested. The response profiles of these two sensors were similar to each other, and were also similar to the responses of the double-stranded DNA sensors made with YO-PRO (FIGS. 10 and 12).

Figure 13A:
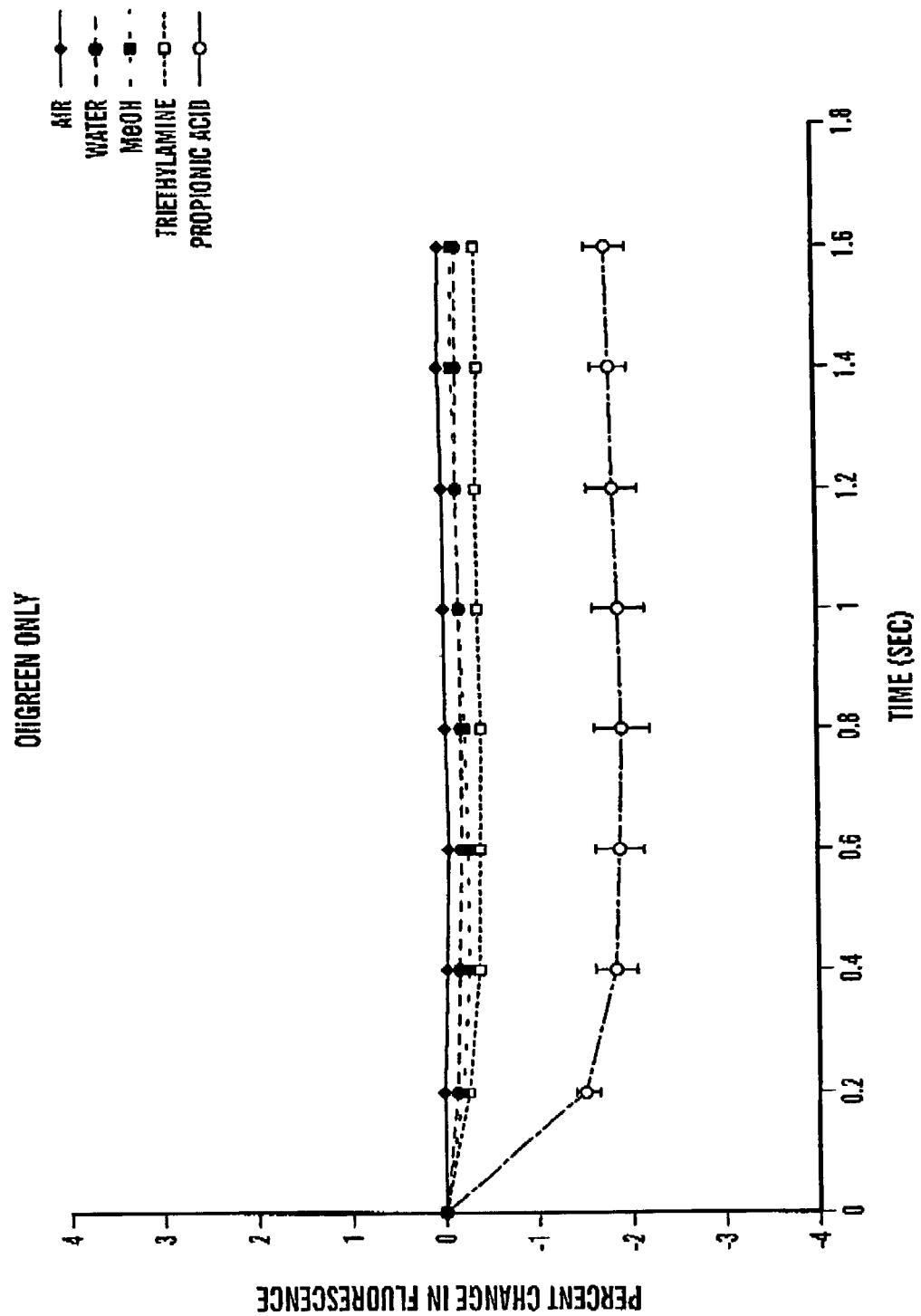
FIGS. 13A–13D show responses of sensors made from different short sequences of single-stranded DNA and Oligreen dye.
Figure 13B:
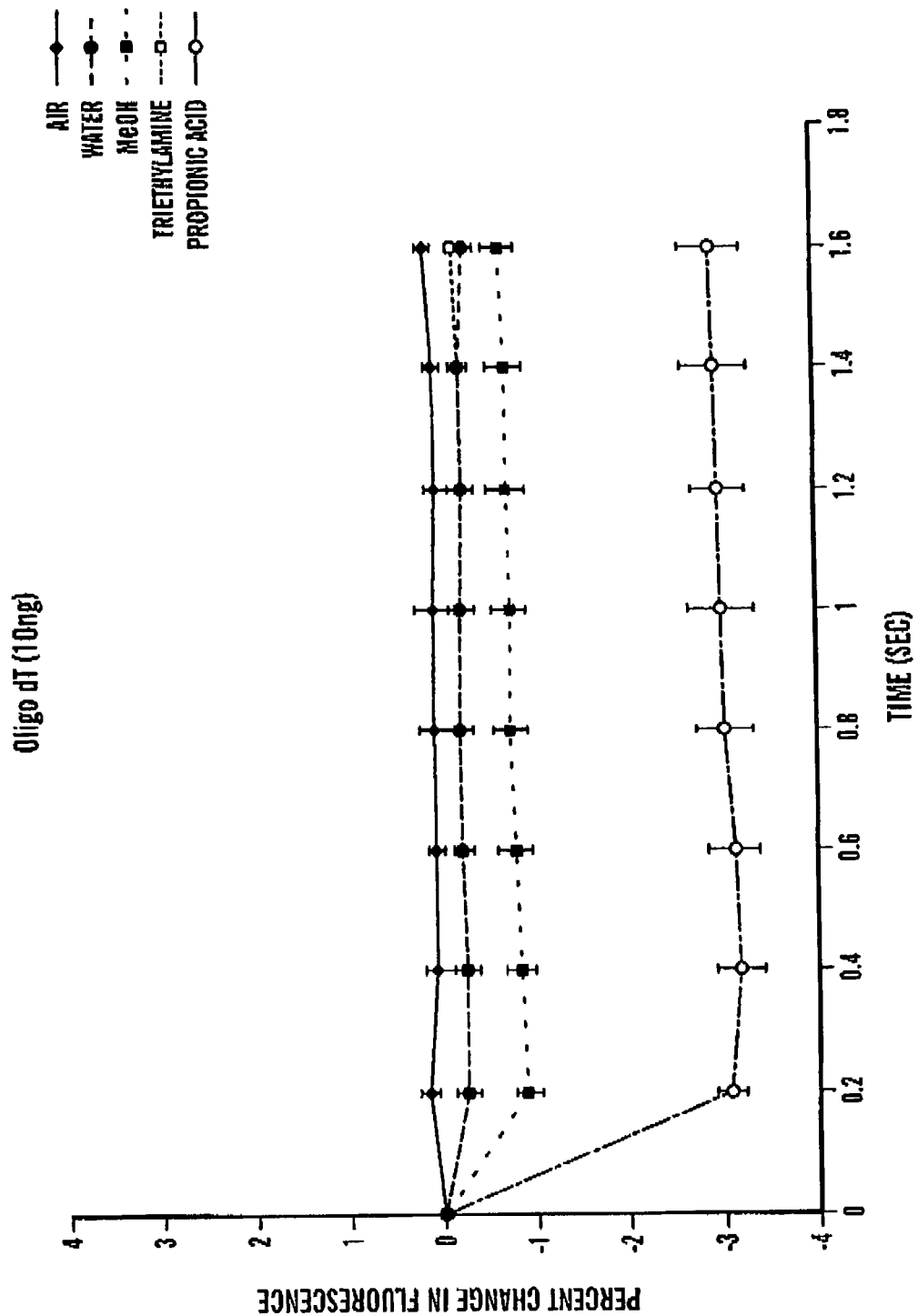
Figure 13C:
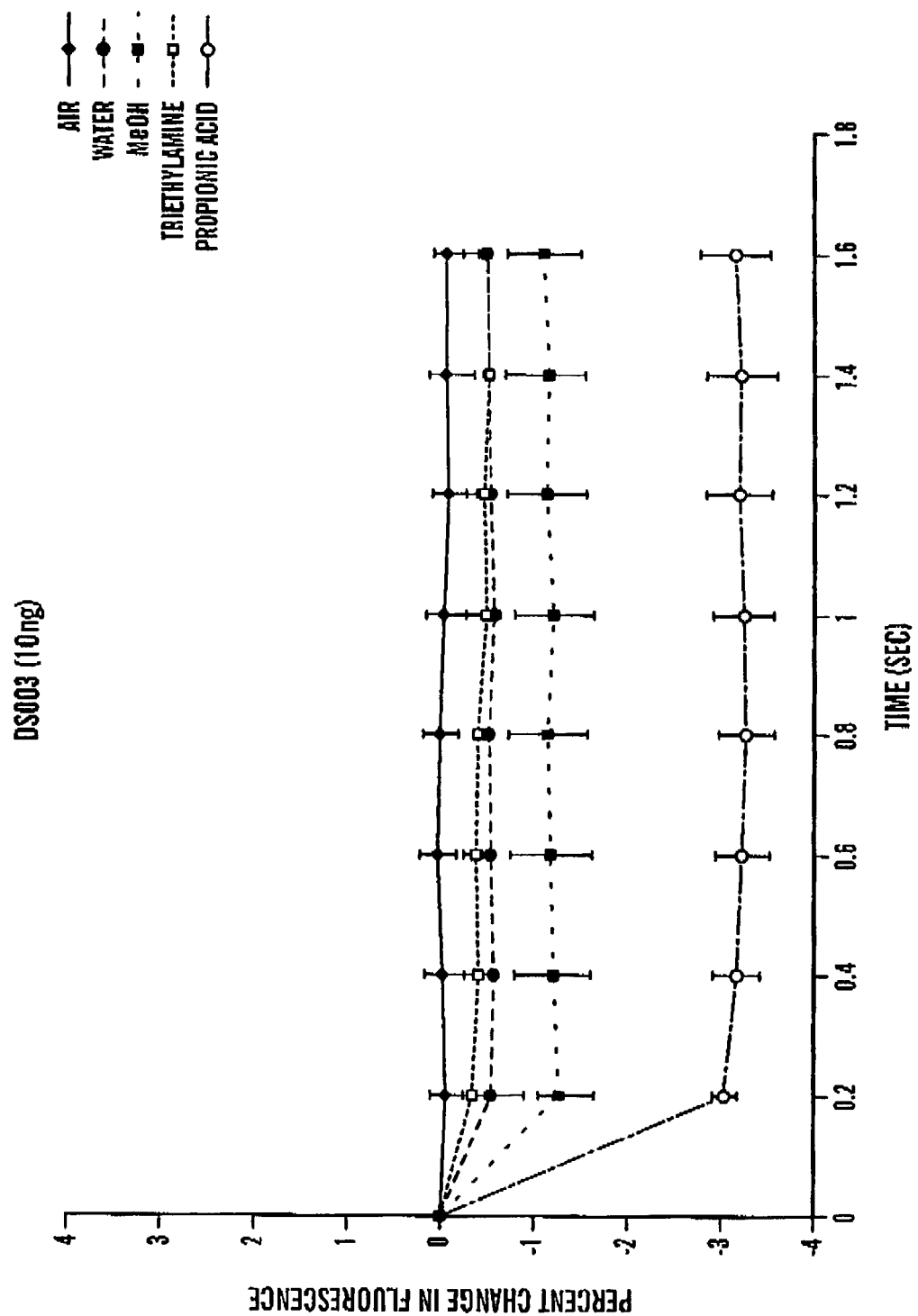
Figure 13D:
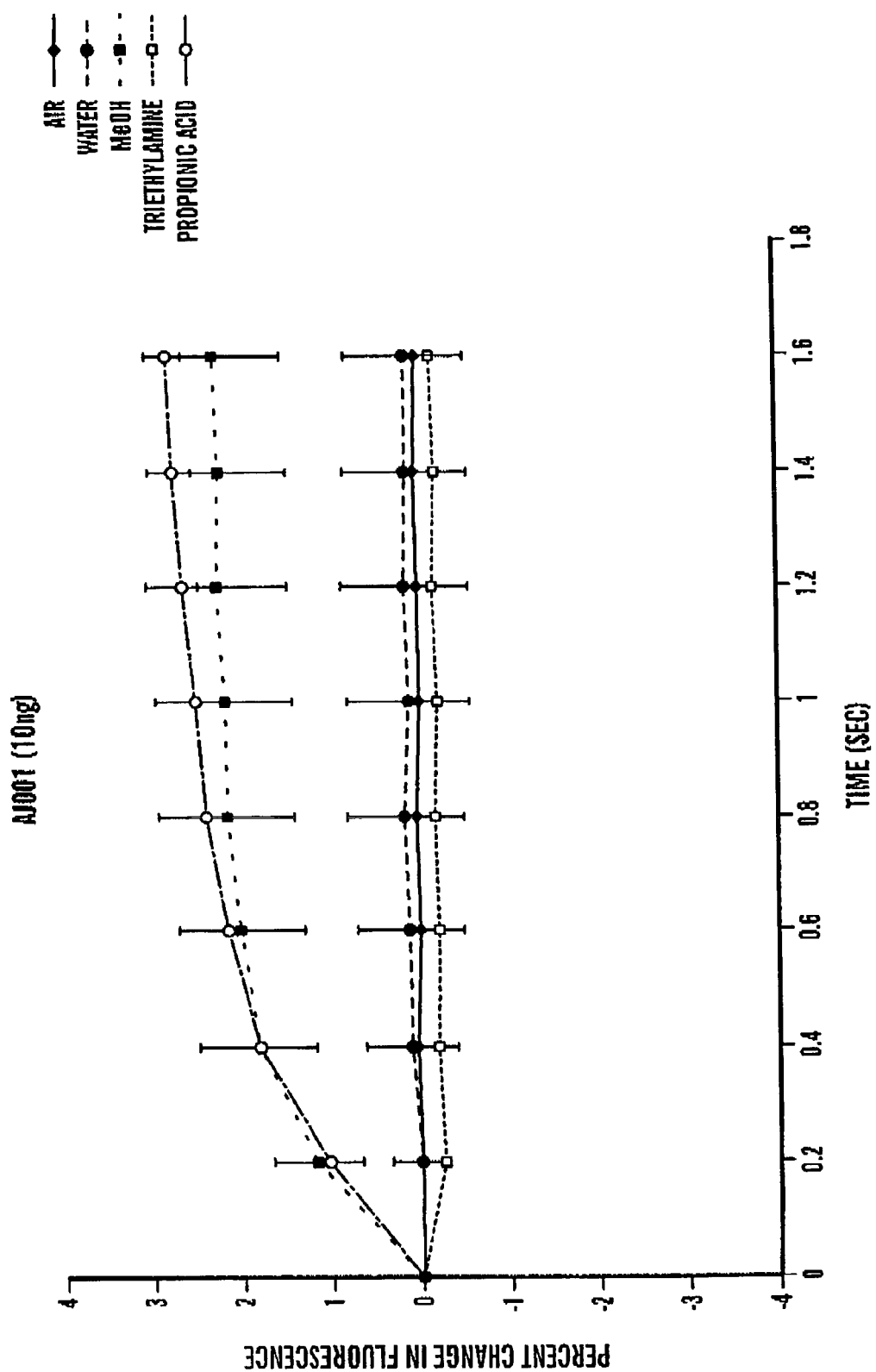

A sensor made with the AJ001 primer sequence, however, had a markedly different odorant response profile (FIG. 13D). This sensor showed an increase in fluorescence in response to propionic acid and methanol, with relatively little change to the other odorants tested. While other DNA-based sensors showed responses to propionic acid, none showed as strong a methanol signal as this AJ001 sensor. The mechanism underlying the AJ001 effect is unknown, but it may be significant that the predicted melting temperatures of the structures formed by this sequence are relatively low (Table 2). Low melting temperatures indicate that the base pair interactions in the short double-stranded regions are relatively weak. Although the structure calculations are made for sequences in aqueous solution, it may be that these structures are maintained after drying.

Example 2

Oligomer sequences LAPP1 and LAPP2 show distinctly different response profiles to this small test set of odorants.

Tested Nucleic Acid Sequences:

```
LAPP1:
5' GAG TCT GTG GAG GAG GTA GTC 3'      (SEQ ID NO 1)

LAPP2:
5' CTT CTG TCT TGA TGT TTG TCA AAC 3'  (SEQ ID NO 2)

LAPPAS:
5' TTT GGC TTT CTG GAA ATG GGC 3'      (SEQ ID NO 3)

LAJ001:
5' ACC AGG ACC TGA CTA AGC AGA T 3'    (SEQ ID NO 4)
```

Oligomers LAPP1, LAPP2, LAPPAS, and LAJ001 were synthesized and labeled at the 5' end with the fluorescent dye Cy3(TM) during synthesis (using Cy3(TM) phosphoramidite from Glen Research). The oligomers were stored in Tris NaCl (10 mM Tris, 50 mM NaCl, pH 8) at 225 ng/ul, then diluted to a concentration of 50 ng/ul in distilled water just before use. Sensors were constructed by applying 20 ul of dilute oligomer solution to 10 mm×12 mm pieces of acid-washed 16xx silkscreen. Sensors were allowed to dry for at least 30 min at room temperature, then attached to supports for testing.

All sensors were mounted in the device and tested simultaneously. All were illuminated with excitation light at 540 nm (30 nm bandwidth). Sensors made with LAPP1, LAPPAS, and LAJ001 were observed at 600 nm (10 nm bandwidth) and LAPP2 was observed at 610 nm (10 nm bandwidth). Vapors from propionic acid, triethylamine, methanol, DNT, and DMMP (dimethyl methylphosphonate, an organophosphate compound that is a simulant for Sarin) were presented to the device using an air dilution olfactometer at the indicated dilutions. For the graphs in the figure, each point in each curve represents the mean sensor response to ten 2 sec sniffs taken at 30 sec intervals; error bars indicate +/- one standard deviation. Signal amplitudes for the odorants are represented as multiples of the signal amplitude of background air (indicated by horizontal dashed line).

Figure 14A:
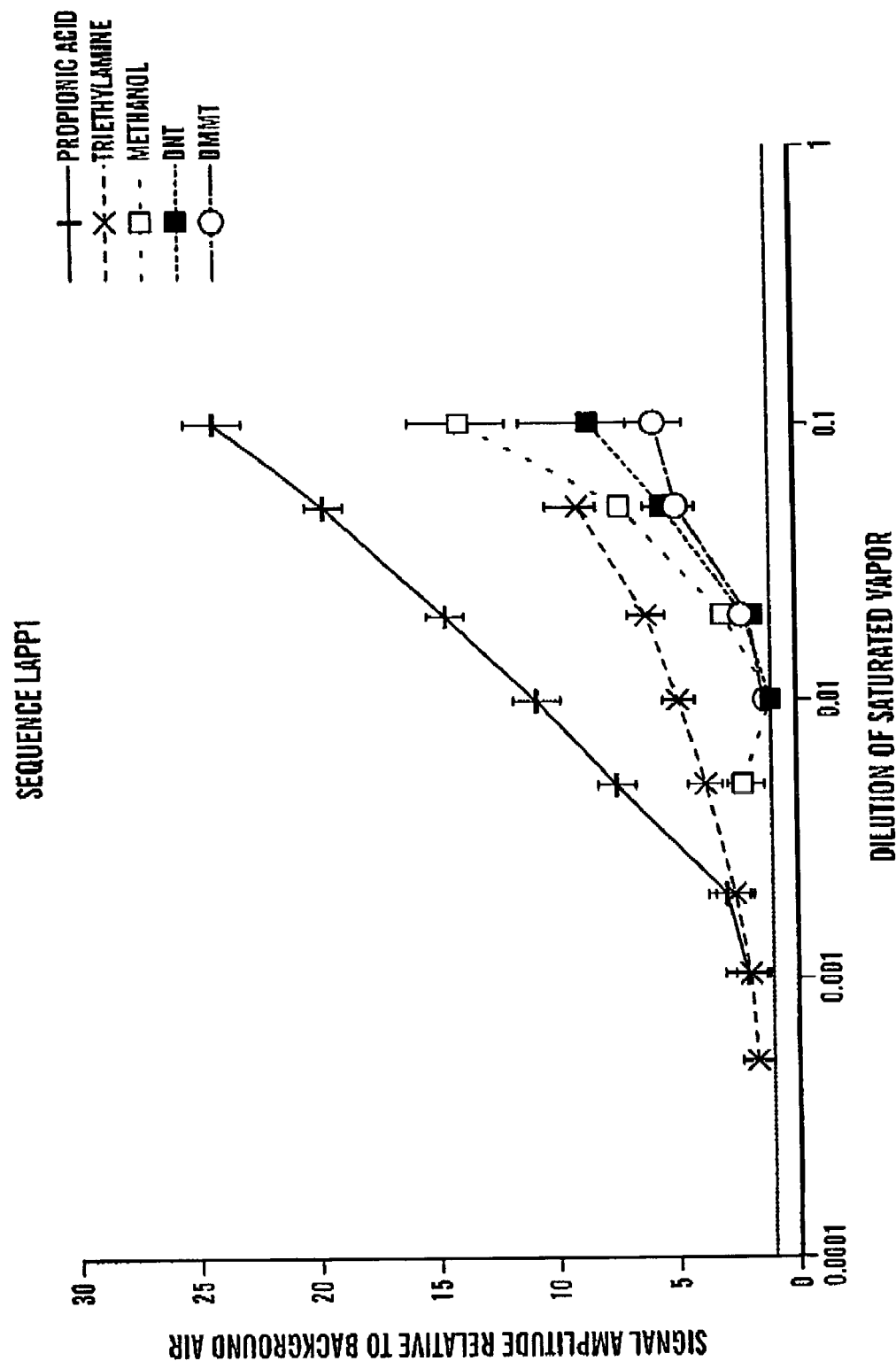
FIGS. 14A–14B show different and distinct responses of two different oligonucleotide sequences to a test set of odorants.
Figure 14B:
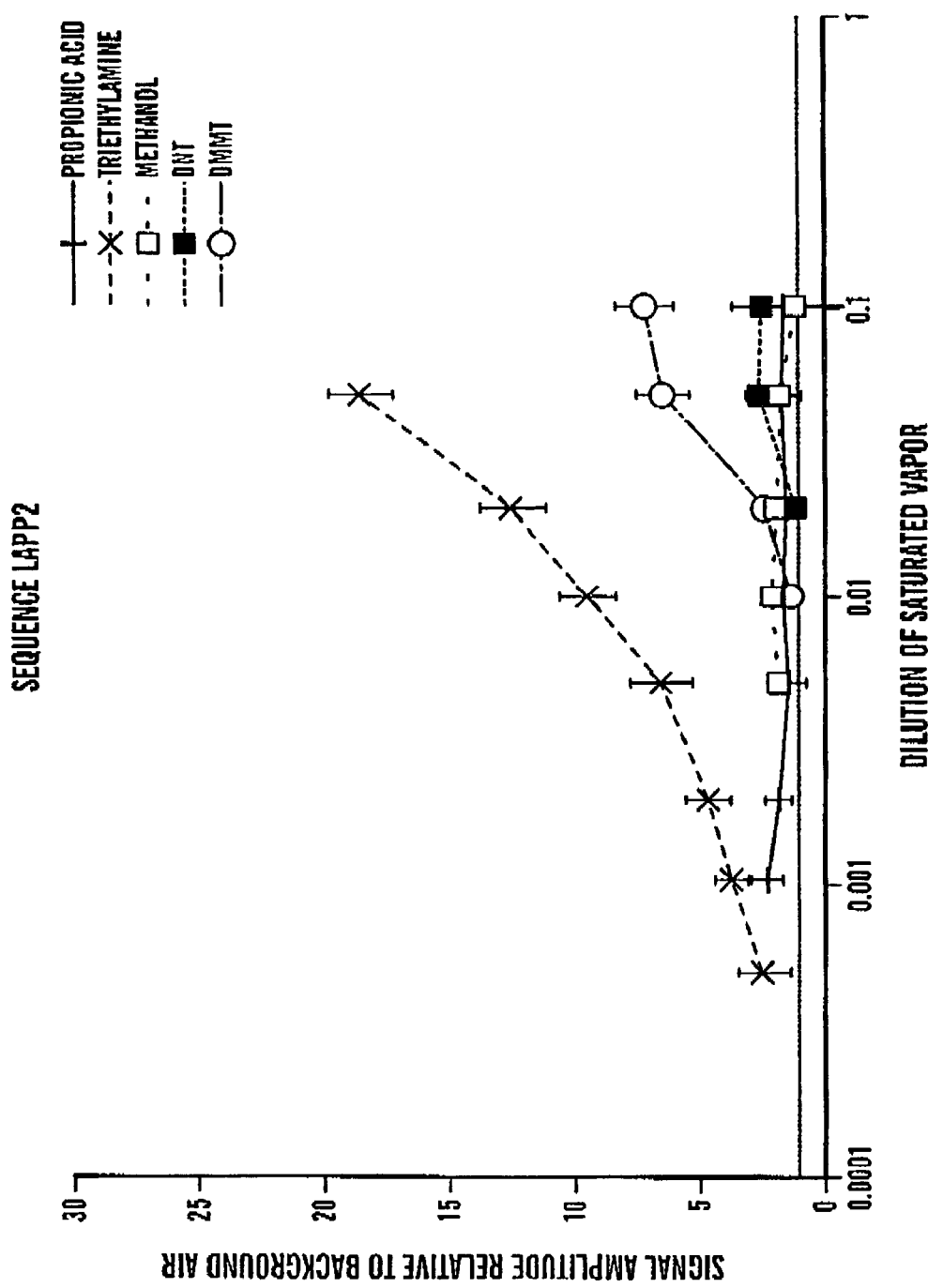

The oligomer sequences LAPP1 and LAPP2 show distinctly different response profiles to this small test set of odorants, as shown in the FIG. 14. The LAPP1 sensor ('A' in Figure) shows good sensitivity to propionic acid and triethylamine (detection limits at dilutions of about 0.001), and less sensitivity to methanol, DNT and DMMP (detection limits at dilutions of about 0.02). In contrast, the LAPP2 sensor (FIG. 14B) shows good sensitivity to triethylamine (detection limit at dilutions of about 0.001), less sensitivity to DMMP (detection limit at dilutions of about 0.02), and almost no response to propionic acid, methanol, or DNT, even at high concentration (0.1 dilution). Sensors made with LAPPAS and LAJ001 sequences showed responses similar to LAPP2, but with smaller amplitudes. These data show that sensors that differ only in nucleotide sequence can exhibit different odorant response profiles.

LAPP1 responds to DNT at dilutions down to 0.02, or approximately 6 ppb, indicating that these sensors are capable of detecting low vapor-phase concentrations.

The references cited throughout the specification are herein incorporated by reference in their entirety.

What is claimed is:

1. A method for detecting a volatile compound in an air sample comprising the steps of:
   a) contacting said air sample with a nucleic acid/fluorophore-based sensor array comprising:
      i) a substrate; and
      ii) a nucleic acid attached to a fluorophore dispersed on said substrate,
         wherein said nucleic acid is dried onto the substrate, and wherein said nucleic acid is attached to a fluorophore providing a characteristic optical response when subjected to excitation light energy in the presence of a volatile compound in the air sample; and
   b) detecting the presence or absence of said volatile compound in the air sample.

2. The method of claim 1, wherein said nucleic acid attached to a fluorophore is dispersed on a plurality of internal and external surfaces within said substrate.

3. The method of claim 1, wherein said contacting further comprises drawing an air sample believed to contain said volatile compound into a sample chamber and exposing said nucleic acid/fluorophore based sensor array to said air sample.

4. The method of claim 1, wherein said detecting further comprises:
   a) illuminating said nucleic acid/fluorophore based senor array with excitation light energy; and
   b) measuring an optical response produced by said nucleic acid/fluorophore based sensor array due to the presence of said volatile compound with a detector means.

5. The method of claim 4, further comprising identifying said volatile compound by employing a pattern-matching algorithm; and comparing said optical response of said nucleic acid/fluorophore based senor array with said characteristic optical response.

6. The method of claim 4, further comprising identifying said volatile compound by providing spatio-temporal response patterns of said optical response; and recognizing said patterns through a method selected from the group consisting of a template matching, neural networks, delay line neural networks, and statistical analysis.

7. The method of claim 1, wherein the air sample is suspected of containing explosive materials.

8. The method of claim 1, wherein the air sample is suspected of containing a chemical weapons agent.

* * * * *